US007951078B2

(12) United States Patent
Scheuner

(10) Patent No.: US 7,951,078 B2
(45) Date of Patent: May 31, 2011

(54) METHOD AND APPARATUS FOR DETERMINING FAMILIAL RISK OF DISEASE

(76) Inventor: Maren Theresa Scheuner, Manhattan Beach, CA (US)

( * ) Notice: Subject to any disclaimer, the term of this patent is extended or adjusted under 35 U.S.C. 154(b) by 1403 days.

(21) Appl. No.: 11/345,862

(22) Filed: Feb. 1, 2006

(65) Prior Publication Data

US 2006/0173717 A1    Aug. 3, 2006

Related U.S. Application Data

(60) Provisional application No. 60/650,076, filed on Feb. 3, 2005.

(51) Int. Cl.
A61B 5/00 (2006.01)

(52) U.S. Cl. ....... 600/300; 705/3; 340/539.12; 128/920; 128/923

(58) Field of Classification Search .................. None
See application file for complete search history.

(56) References Cited

U.S. PATENT DOCUMENTS

| | | | |
|---|---|---|---|
| 5,692,501 A | 12/1997 | Minturn | |
| 2002/0184055 A1 | 12/2002 | Naghavi et al. | |
| 2003/0120515 A1 | 6/2003 | Geller | |
| 2003/0170638 A1 | 9/2003 | White et al. | |
| 2003/0204418 A1 | 10/2003 | Ledley | |
| 2004/0153249 A1* | 8/2004 | Zhang et al. | 702/19 |
| 2009/0018863 A1 | 1/2009 | Yoon et al. | |

FOREIGN PATENT DOCUMENTS

WO    WO 2006/084195 A2    8/2006

OTHER PUBLICATIONS

Maren T. Scheuner, et al., "Family History: A Comprehensive Genetic Risk Assessment Method for the Chronic Conditions of Adulthood", American Journal of Medical Genetics, vol. 71, 1997 (pp. 315-324).*
Jon Emery, et al., "Computer Support for Interpreting Family Histories of Breast and Ovarian Cancer in Primary Care: Comparative Study with Simulated Cases", BMJ, vol. 321, Jul. 1, 2000 (pp. 28-32).
"What is CancerGene?", Southwestern the University of Texas Southwestern Medical Center at Dallas, Breast Cancer Risk Evaluation, Jan. 30, 2006, Internet article http://www3.utsouthwestern.edu/cancergene/cancergene.htm (5 pgs.).

(Continued)

*Primary Examiner* — Eric F Winakur
*Assistant Examiner* — Bobby Soriano
(74) *Attorney, Agent, or Firm* — Blakely, Sokoloff, Taylor & Zafman LLP

(57) ABSTRACT

Personal and family health history information can be used to assess familial risk of disease. For example, information can be collected about the disease history of a person and the person's first- and second-degree relatives and then analyzed to determine the familial risk of common diseases such as coronary heart disease, stroke, type 2 diabetes, and colorectal, breast, and ovarian cancer. Assessed familial risk of disease can then be used by researchers to better estimate the contribution of personal history and family history to the etiology and natural history of a disease of interest, and by consumers and health professionals to determine recommendations for disease management, prevention and screening that are personalized and targeted to the familial risk. Other embodiments are also described and claimed.

9 Claims, 25 Drawing Sheets

For female user, personal history of both early-onset breast cancer and ovarian cancer at any age, and . . .

| | One 1st deg rel w/ early breast and ovarian | One 1st deg rel w/ late breast and ovarian | One 1st deg FEMALE rel w/ early breast | One 1st deg MALE rel w/ early breast | One 1st deg rel w/ ovarian | One 1st deg MALE rel w/ late breast | TWO 1st deg FEMALE rel w/ late breast | One 1st deg FEMALE rel w/ late breast | No 1st deg rel w/ breast or ovarian |
|---|---|---|---|---|---|---|---|---|---|
| One 1st deg rel w/ early breast and ovarian | 1-001 H a, c, e, i, k | 1-002 H a, c, e, i, k | 1-003 H a, c, e, i, k | 1-004 H a, c, d, e, i, k | 1-005 H a, c, e, f, k | 1-006 H a, c, d, e, i, k | 1-007 H a, c, e, i, k | 1-008 H a, c, e, i, k | 1-009 H a, c, e, f, k |
| One 1st deg rel w/ late breast and ovarian | H a, c, e, i, k | 1-010 H a, c, e, i, k | 1-011 H a, c, e, i, k | 1-012 H a, c, d, e, i, k | 1-013 H a, c, e, f, k | 1-014 H a, c, d, e, i, k | 1-015 H a, c, e, i, k | 1-016 H a, c, e, i, k | 1-017 H a, c, e, f, k |
| One 1st deg FEMALE rel w/ early breast | H a, c, e, i, k | H a, c, e, i, k | 1-018 H a, e, i, k | 1-019 H a, d, e, i, k | 1-020 H a, b, e, f, k | 1-021 H a, d, e, i, k | 1-022 H a, e, i, k | 1-023 H a, e, i, k | 1-024 H a, e, f, k |
| One 1st deg MALE rel w/ early breast | H a, c, d, e, i, k | H a, c, d, e, i, k | H a, d, e, i, k | 1-025 H a, d, e, i, k | 1-026 H a, b, d, e, f, k | 1-027 H a, d, e, i, k | 1-028 H a, d, e, i, k | 1-029 H a, d, e, i, k | 1-030 H a, d, e, f, k |
| One 1st deg rel w/ ovarian | H a, c, e, f, k | H a, c, e, f, k | H a, b, e, f, k | H a, b, d, e, f, k | 1-031 H a, c, e, k | 1-032 H a, b, d, e, f, k | 1-033 H a, b, e, i, k | 1-034 H a, b, e, f, k | 1-035 H a, b, e, k |
| One 1st deg MALE rel w/ late breast | H a, c, d, e, f, k | H a, c, d, e, f, k | H a, d, e, f, k | H a, d, e, f, k | H a, b, d, e, f, k | 1-036 H a, d, e, f, k | 1-037 H a, d, e, f, i, k | 1-038 H a, d, e, f, k | 1-039 H a, d, e, f, k |
| Two 1st deg FEMALE rel w/ late breast | H a, e, i, k | H a, e, i, k | H a, e, i, k | H a, d, e, i, k | H a, b, e, i, k | H a, d, e, i, k | 1-040 H a, e, i, k | 1-041 H a, e, i, k | 1-042 H a, e, i, k |
| One 1st deg FEMALE rel w/ late breast | H a, c, e, i, k | H a, c, e, i, k | H a, e, i, k | H a, d, e, i, k | H a, b, e, f, k | H a, d, e, i, k | H a, e, i, k | 1-043 H a, e, i, k | 1-044 H a, e, f, k |
| No 1st deg rel with breast or ovarian | H a, c, e, f, k | H a, c, e, f, k | H a, e, f, k | H a, d, e, f, k | H a, b, e, k | H a, d, e, f, k | H a, e, i, k | H a, e, f, k | 1-045 H a, e, k |

OTHER PUBLICATIONS

"Breast Cancer Risk Assessment Tool", National Cancer Institute, Software 2000 iCARDINAL, Internet article http://bcra.nci.nih.gov/brc/ (5 pgs.).

PCT International Search Report (dated Aug. 22, 2007), International Application No. PCT/US06/03792—International Filing Date Feb. 2, 2006 (9 pages).

Acheson, Louise S., et al., "Validation of a Self-Administered, Computerized Tool for Collecting and Displaying the Family History of Cancer", Journal of Clinical Oncology, Original Report, vol. 24, No. 34, Dec. 1, 2006, (pp. 5395-5402).

Acheson, MS, MD, Louise S., et al., "Family History and Perceptions About Risk and Prevention for Chronic Diseases in Primary Care: A Report from the Family Healthware™ Impact Trial", Genetics in Medicine, vol. 12, No. 4, Apr. 2010, (doi: 10.1097/GIM.0b013e3181d56ae6), (pp. 212-218).

Coulson, A. S., et al., "RAGs: A Novel Approach to Computerized Genetic Risk Assessment and Decision Support from Pedigrees", Advanced Computation Laboratory, Imperial Cancer Research Fund, London, United Kingdom, Method Inform Med Apr. 2001, vol. 40, (pp. 315-322).

Emery, Jon, et al., "Computer Support for Recording and Interpreting Family Histories of Breast and Ovarian Cancer in Primary Care (RAGs): Qualitative Evaluation with Simulated Patients", BMJ, vol. 319, Jul. 3, 1999, (pp. 32-36).

Emery, J., "The GRAIDS Trial: The Development and Evaluation of Computer Decision Support for Cancer Genetic Risk Assessment in Primary Care", Annals of Human Biology, Mar.-Apr. 2005, vol. 32(2), ISSN 0301-4460, (doi: 10.1080/03014460500074921), (pp. 218-227).

Hampel, H., et al., "Referral for Cancer Genetics Consultation: A Review and Compilation of Risk Assessment Criteria", Medical Genetics in Practice, J Med Genet 2004, vol. 41 (doi: 10.1136/jmg.2003.010918), (pp. 81-91).

Hariri, PhD, Susan, et al., "Family History of Type 2 Diabetes: A Population-Based Screening Tool for Prevention?", Article, Genetics in Medicine, Feb. 2006, vol. 8, No. 2, (pp. 102-108).

Henderson, MD, L. B., et al., "A Familial Risk Profile for Osteoporosis", Article, Genetics in Medicine, Jul./Aug. 2000, vol. 2, No. 4, (pp. 222-225).

Qureshi, M.B.B.S., D.M., Nadeem, et al., "Collection and Use of Cancer Family History in Primary Care", Evidence Report/Technology Assessment, No. 159, AHRQ Publication No. 08-E001, Oct. 2007, ( Whole Document).

Scheuner, Maren T., et al., "Contribution of Mendelian Disorders to Common Chronic Disease: Opportunities for Recognition, Intervention, and Prevention", Article, American Journal of Medical Genetics Part C (Semin. Med. Genet.) 125C, published 2004 Wiley-Liss, Inc., (pp. 50-65).

Scheuner, MD, MPH, Maren, "Clinical Application of Genetic Risk Assessment Strategies for Coronary Artery Disease: Genotypes, Phenotypes, and Family History", Primary Care: Clinics in Office Practice, vol. 31, 2004, (pp. 711-737).

Scheuner, MD, MPH, Maren, et al., "Expanding the Definition of a Positive Family History for Early-Onset Coronary Heart Disease", Genetics in Medicine, Aug. 2006, vol. 8, No. 8, (pp. 491-501).

Scheuner, MD, MPH, Maren, et al., "Familial Risk Assessment for Early-Onset Coronary Heart Disease", Article, Genetics in Medicine, Aug. 2006, vol. 8, No. 8, (pp. 525-531).

Scheuner, MD, MPH, Maren, "Family History: Where to Go From Here", Editorial, Genetics in Medicine, Mar./Apr. 2003, vol. 5, No. 2, (pp. 66-68).

Scheuner, MD, MPH, Maren, et al., "General Cardiovascular Risk Profile Identifies Advanced Coronary Artery Calcium and is Improved by Family History", Circ Cardiovasc Genet., vol. 3, Feb. 2010, (pp. 97-105).

Scheuner, MD, MPH, Maren, "Genetic Evaluation for Coronary Artery Disease", Review, Genetics in Medicine, Jul./Aug. 2003, vol. 5, No. 4, (pp. 269-285).

Scheuner, MD, MPH, Maren, et al., "Population Prevalence of Familial Cancer and Common Hereditary Cancer Syndromes. The 2005 Califronia Health Interview Summary", Article, Genetics in Medicine, vol. 12, No. 11, Nov. 2010 (doi: 10.1097/GIM.0b013e181f30e9e), (pp. 726-735).

Scheuner, MD, MPH, Maren, et al., "Relation of Familial Patterns of Coronary Heart Disease, Stroke, and Diabetes to Subclinical Atherosclerosis: The Multi-Ethnic Study of Atherosclerosis", Article, Genetics in Medicine, Dec. 2008, vol. 10, No. 12, (pp. 879-887).

Simon, PhD, Christian, et al., "Patient Interest in Recording Family Histories of Cancer Via the Internet", Genetics in Medicine, copyright American College of Medical Genetics, Dec. 2008, vol. 10, No. 12, (pp. 895-902).

Sweet, Kevin M., et al., "Identification and Referral of Families at High Risk for Cancer Susceptibility", Journal of Clinical Oncology, vol. 20, No. 2, Jan. 15, 2002, (pp. 528-537).

Westman, Judith, et al., "Efficacy of a Touchscreen Computer Based Family Cancer History Questionnaire and Subsequent Cancer Risk Assessment", Human Cancer Genetics Program, Arthur G. James Cancer Hospital and Richard J. Solove Research Institute, Comprehensive Cancer Center, The Ohio State University, Columbus, Ohio, USA, Medical Genet 2000, vol. 37, (pp. 354-360).

Yoon, SCD, Paula W., et al., "Research Priorities for Evaluating Family History in the Prevention of Common Chronic Diseases", Theme Articles, Am J Prev Med 2003, vol. 24(2), Elsevier (doi: 10.1016/S0749-3797(02)00585-8), (pp. 128-135).

Yoon, SCD, MPH, Paula W., et al., "Can Family History be Used as a Tool for Public Health and Preventive Medicine?", Commentary, Genetics in Medicine, Jul./Aug. 2002, vol. 4, No. 4, (pp. 304-310).

Yoon, SCD, MPH, Paula W., et al., "Developing Family Healthware, a Family History Screening Tool to Prevent Common Chronic Diseases", Tools and Techniques, Preventing Chronic Disease Public Health Research, Practice, and Policy, Jan. 2009, vol. 6, No. 1, (pp. 1-11).

O'Neill, MA, MS, PhD, Suzanne M., et al., "Familial Risk for Common Diseases in Primary Care The Family Healthware™ Impact Trial", American Journal of Preventive Medicine, 2009, vol. 36(6), (doi: 10.1016/j.amepre.2009.03.002), (pp. 506-514).

\* cited by examiner

For female user, personal history of both early-onset breast cancer and ovarian cancer at any age, and ...

| | One 1st deg rel w/ early breast and ovarian | One 1st deg rel w/ late breast and ovarian | One 1st deg FEMALE rel w/ early breast | One 1st deg MALE rel w/ early breast | One 1st deg rel w/ ovarian | One 1st deg MALE rel w/ late breast | TWO 1st deg FEMALE rel w/ late breast | One 1st deg FEMALE rel w/ late breast | No 1st deg rel w/ breast or ovarian |
|---|---|---|---|---|---|---|---|---|---|
| One 1st deg rel w/ early breast and ovarian | 1-001 H a, c, e, i, k | 1-002 H a, c, e, i, k | 1-003 H a, c, e, i, k | 1-004 H a, c, d, e, i, k | 1-005 H a, c, e, f, k | 1-006 H a, c, d, e, i, k | 1-007 H a, c, e, i, k | 1-008 H a, c, e, i, k | 1-009 H a, c, e, f, k |
| One 1st deg rel w/ late breast and ovarian | H a, c, e, i, k | 1-010 H a, c, e, i, k | 1-011 H a, c, e, i, k | 1-012 H a, c, d, e, i, k | 1-013 H a, c, e, f, k | 1-014 H a, c, d, e, i, k | 1-015 H a, c, e, i, k | 1-016 H a, c, e, i, k | 1-017 H a, c, e, f, k |
| One 1st deg FEMALE rel w/ early breast | H a, c, e, i, k | H a, c, e, i, k | 1-018 H a, e, i, k | 1-019 H a, d, e, i, k | 1-020 H a, c, e, f, k | 1-021 H a, d, e, i, k | 1-022 H a, e, i, k | 1-023 H a, e, i, k | 1-024 H a, e, f, k |
| One 1st deg MALE rel w/ early breast | H a, c, d, e, i, k | H a, c, d, e, i, k | H a, d, e, i, k | 1-025 H a, d, e, i, k | 1-026 H a, b, d, e, f, k | 1-027 H a, d, e, i, k | 1-028 H a, d, e, i, k | 1-029 H a, d, e, i, k | 1-030 H a, d, e, f, k |
| One 1st deg rel w/ ovarian | H a, c, e, f, k | H a, c, e, f, k | H a, b, e, f, k | H a, b, d, e, f, k | 1-031 H a, c, e, k | 1-032 H a, b, d, e, f, k | 1-033 H a, b, e, i, k | 1-034 H a, b, e, i, k | 1-035 H a, b, e, k |
| One 1st deg MALE rel w/ late breast | H a, c, d, e, f, k | H a, c, d, e, f, k | H a, d, e, f, k | H a, d, e, f, k | H a, b, d, e, f, k | 1-036 H a, b, d, e, f, k | 1-037 H a, d, e, f, i, k | 1-038 H a, b, e, f, k | 1-039 H a, d, e, f, k |
| Two 1st deg FEMALE rel w/ late breast | H a, c, e, i, k | H a, c, e, i, k | H a, d, e, i, k | H a, d, e, i, k | H a, b, d, e, f, k | H a, d, e, f, k | 1-040 H a, e, i, k | 1-041 H a, e, i, k | 1-042 H a, d, e, f, k |
| One 1st deg FEMALE rel w/ late breast | H a, c, e, i, k | H a, c, e, i, k | H a, e, i, k | H a, d, e, i, k | H a, b, e, i, k | H a, d, e, i, k | H a, e, i, k | 1-043 H a, e, i, k | 1-044 H a, e, i, k |
| No 1st deg rel with breast or ovarian | H a, c, e, f, k | H a, c, e, f, k | H a, e, f, k | H a, d, e, f, k | H a, b, e, k | H a, d, e, f, k | H a, e, i, k | H a, e, f, k | 1-045 H a, e, k |

FIG. 7

For female user, personal history of both early-onset breast cancer and ovarian cancer at any age, and …

| | One 2nd deg rel w/ early breast and ovarian | One 2nd deg rel w/ late breast and ovarian | One 2nd deg FEMALE rel w/ early breast | One 2nd deg MALE rel w/ early breast | One 2nd deg rel w/ ovarian | One 2nd deg MALE rel w/ late breast | TWO 2nd deg FEMALE rel w/ late breast | One 2nd deg FEMALE rel w/ late breast | No 2nd deg rel w/ breast or ovarian |
|---|---|---|---|---|---|---|---|---|---|
| One 1st deg rel w/ early breast and ovarian | 1-046 H a,c,e,i,k | 1-047 H a,c,e,i,k | 1-048 H a,c,e,i,k | 1-049 H a,c,d,e,i,k | 1-050 H a,c,e,f,k | 1-051 H a,c,d,e,i,k | 1-052 H a,c,e,i,k | 1-053 H a,c,e,i,k | H a,c,e,f,k |
| One 1st deg rel w/ late breast and ovarian | 1-054 H a,c,e,i,k | 1-055 H a,c,e,i,k | 1-056 H a,c,e,i,k | 1-057 H a,c,d,e,i,k | 1-058 H a,c,e,f,k | 1-059 H a,c,d,e,i,k | 1-060 H a,c,e,i,k | 1-061 H a,c,e,i,k | H a,c,e,f,k |
| One 1st deg FEMALE rel w/ early breast | 1-062 H a,c,e,i,k | 1-063 H a,c,e,i,k | 1-064 H a,e,i,k | 1-065 H a,d,e,i,k | 1-066 H a,b,e,f,k | 1-067 H a,d,e,i,k | 1-068 H a,e,i,k | 1-069 H a,e,i,k | H a,e,f,k |
| One 1st deg MALE rel w/ early breast | 1-070 H a,c,d,e,i,k | 1-071 H a,c,d,e,i,k | 1-072 H a,d,e,i,k | 1-073 H a,d,e,i,k | 1-074 H a,b,d,e,f,k | 1-075 H a,d,e,i,k | 1-076 H a,d,e,i,k | 1-077 H a,d,e,i,k | H a,d,e,f,k |
| One 1st deg rel w/ ovarian | 1-078 H a,c,e,f,k | 1-079 H a,c,e,f,k | 1-080 H a,b,e,f,k | 1-081 H a,b,d,e,f,k | 1-082 H a,c,e,k | 1-083 H a,b,d,e,f,k | 1-084 H a,b,e,i,k | 1-085 H a,b,e,f,k | H a,b,e,k |
| One 1st deg MALE rel w/ late breast | 1-086 H a,c,e,f,k | 1-087 H a,c,d,e,i,k | 1-088 H a,d,e,i,k | 1-089 H a,d,e,i,k | 1-090 H a,c,e,k | 1-091 H a,d,e,i,k | 1-092 H a,d,e,i,k | 1-093 H a,b,e,f,k | H a,d,e,f,k |
| TWO 1st deg FEMALE rel w/ late breast | 1-094 H a,c,d,e,i,k | 1-095 H a,c,d,e,i,k | 1-096 H a,d,e,i,k | 1-097 H a,d,e,i,k | 1-098 H a,b,d,e,f,k | 1-099 H a,d,e,i,k | 1-100 H a,d,e,i,k | 1-101 H a,d,e,i,k | H a,d,e,f,k |
| One 1st deg FEMALE rel w/ late breast | 1-102 H a,c,e,i,k | 1-103 H a,c,e,i,k | 1-104 H a,e,i,k | 1-105 H a,d,e,i,k | 1-106 H a,b,e,f,k | 1-107 H a,d,e,i,k | 1-108 H a,e,i,k | 1-109 H a,e,i,k | H a,e,f,k |
| No 1st deg rel with breast or ovarian | H a,c,e,f,k | H a,c,e,f,k | H a,e,f,k | H a,d,e,f,k | H a,b,e,k | H a,d,e,f,k | H a,e,f,k | H a,e,f,k | H a,e,k |

FIG. 8

For female user, personal history of both early-onset breast cancer and ovarian cancer at any age, and ...

| | One 2nd deg rel w/ early breast and ovarian | One 2nd deg rel w/ late breast and ovarian | One 2nd deg FEMALE rel w/ early breast | One 2nd deg MALE rel w/ early breast | One 2nd deg rel w/ ovarian | One 2nd deg MALE rel w/ late breast | TWO 2nd deg FEMALE rel w/ late breast | One 2nd deg FEMALE rel w/ late breast | No 2nd deg rel w/ breast or ovarian |
|---|---|---|---|---|---|---|---|---|---|
| One 2nd deg rel w/ early breast and ovarian | 1-110 H a, c, e, i, k | 1-111 H a, c, e, i, k | 1-112 H a, c, e, i, k | 1-113 H a, c, d, e, i, k | 1-114 H a, c, e, f, k | 1-115 H a, c, d, e, i, k | 1-116 H a, c, e, i, k | 1-117 H a, c, e, i, k | 1-118 H a, c, e, f, k |
| One 2nd deg rel w/ late breast and ovarian | H a, c, e, i, k | 1-119 H a, c, e, i, k | 1-120 H a, c, e, i, k | 1-121 H a, c, d, e, i, k | 1-122 H a, c, e, f, k | 1-123 H a, c, d, e, i, k | 1-124 H a, c, e, i, k | 1-125 H a, c, e, i, k | 1-126 H a, c, e, f, k |
| One 2nd deg FEMALE rel w/ early breast | H a, c, e, i, k | H a, c, e, i, k | 1-127 H a, e, i, k | 1-128 H a, d, e, i, k | 1-129 H a, b, e, f, k | 1-130 H a, d, e, i, k | 1-131 H a, e, i, k | 1-132 H a, e, i, k | 1-133 H a, e, f, k |
| One 2nd deg MALE rel w/ early breast | H a, c, d, e, i, k | H a, c, d, e, i, k | H a, d, e, i, k | 1-134 H a, d, e, i, k | 1-135 H a, b, d, e, f, k | 1-136 H a, d, e, i, k | 1-137 H a, d, e, i, k | 1-138 H a, d, e, i, k | 1-139 H a, d, e, f, k |
| One 2nd deg rel w/ ovarian | H a, c, e, f, k | H a, c, e, f, k | H a, b, d, e, f, k | H a, b, d, e, f, k | 1-140 H a, c, e, k | 1-141 H a, b, d, e, f, k | 1-142 H a, b, e, i, k | 1-143 H a, b, e, f, k | 1-444 H a, b, e, k |
| One 2nd deg MALE rel w/ late breast | H a, c, d, e, i, k | H a, c, d, e, i, k | H a, d, e, i, k | H a, d, e, i, k | H a, b, d, e, f, k | 1-145 H a, d, e, i, k | 1-146 H a, d, e, i, k | 1-147 H a, d, e, i, k | 1-148 H a, d, e, f, k |
| TWO 2nd deg FEMALE rel w/ late breast | H a, c, e, i, k | H a, c, e, i, k | H a, e, i, k | H a, d, e, i, k | H a, b, e, i, k | H a, d, e, i, k | 1-149 H a, e, i, k | 1-150 H a, e, i, k | 1-151 H a, e, i, k |
| One 2nd deg FEMALE rel w/ late breast | H a, c, e, i, k | H a, c, e, i, k | H a, e, i, k | H a, d, e, i, k | H a, b, e, f, k | H a, d, e, i, k | H a, e, i, k | 1-152 H a, e, i, k | 1-153 H a, e, f, k |
| No 2nd deg rel with breast or ovarian | H a, c, e, f, k | H a, c, e, f, k | H a, e, f, k | H a, d, e, f, k | H a, b, e, k | H a, d, e, f, k | H a, e, i, k | H a, e, f, k | 1-154 H a, e, k |

FIG. 9

| For female user, personal history of both late-onset breast cancer and ovarian cancer at any age, and ... | One 1st deg rel w/ early breast and ovarian | One 1st deg rel w/ late breast and ovarian | One 1st deg FEMALE rel w/ early breast | One 1st deg MALE rel w/ early breast | One 1st deg rel w/ ovarian | One 1st deg MALE rel w/ late breast | TWO 1st deg FEMALE rel w/ late breast | One 1st deg FEMALE rel w/ late breast | No 1st deg rel w/ breast or ovarian |
|---|---|---|---|---|---|---|---|---|---|
| One 1st deg rel w/ early breast and ovarian | 2-001 H a, c, e, i, k | 2-002 H a, c, e, i, k | 2-003 H a, c, e, i, k | 2-004 H a, c, d, e, i, k | 2-005 H a, c, e, f, k | 2-006 H a, c, d, e, i, k | 2-007 H a, c, e, i, k | 2-008 H a, c, e, i, k | 2-009 H a, c, e, f, k |
| One 1st deg rel w/ late breast and ovarian | H a, c, e, i, k | 2-010 H a, c, i, k | 2-011 H a, c, e, i, k | 2-012 H a, c, d, e, i, k | 2-013 H a, c, f, k | 2-014 H a, c, d, i, k | 2-015 H a, c, i, k | 2-016 H a, c, i, k | 2-017 H a, c, f, k |
| One 1st deg FEMALE rel w/ early breast | H a, c, d, e, i, k | H a, c, e, i, k | 2-018 H a, e, i, k | 2-019 H a, c, d, e, i, k | 2-020 H a, b, e, f, k | 2-021 H a, d, e, i, k | 2-022 H a, e, i, k | 2-023 H a, e, i, k | 2-024 H a, e, f, k |
| One 1st deg MALE rel w/ early breast | H a, c, d, e, i, k | H a, c, d, e, i, k | H a, d, e, i, k | H a, d, e, i, k | 2-025 H a, b, d, e, f, k | 2-026 H a, d, e, i, k | 2-027 H a, d, e, i, k | 2-028 H a, d, e, i, k | 2-029 H a, d, e, f, k |
| One 1st deg rel w/ ovarian | H a, c, e, f, k | H a, c, f, k | H a, b, e, f, k | H a, b, d, e, f, k | 2-031 H a, c, k | 2-032 H a, b, d, f, k | 2-033 H a, b, i, k | 2-034 H a, b, f, k | 2-035 H a, c, k |
| One 1st deg MALE rel w/ late breast | H a, c, d, e, i, k | H a, c, d, i, k | H a, d, e, i, k | H a, d, e, i, k | H a, b, d, d, f, k | 2-036 H a, d, i, k | 2-037 H a, d, i, k | 2-038 H a, d, i, k | 2-039 H a, d, f, k |
| Two 1st deg FEMALE rel w/ late breast | H a, c, e, i, k | H a, c, i, k | H a, e, i, k | H a, d, e, i, k | H a, b, i, k | H a, d, f, i, k | 2-040 H a, i, k | 2-041 H a, i, k | 2-042 H a, i, k |
| One 1st deg FEMALE rel w/ late breast | H a, c, e, i, k | H a, c, i, k | H a, e, i, k | H a, d, e, i, k | H a, b, f, k | H a, d, i, k | H a, i, k | 2-043 H a, i, k | 2-044 H a, f, k |
| No 1st deg rel w/ breast | H a, c, e, f, k | H a, c, f, k | H a, e, f, k | H a, d, e, f, k | H a, c, k | H a, d, f, k | H a, i, k | H a, f, k | 2-045 H a, k |

FIG. 10

For female user, personal history of both late-onset breast cancer and ovarian cancer at any age, and …

| | One 2nd deg rel w/ early breast and ovarian | One 2nd deg rel w/ late breast and ovarian | One 2nd deg FEMALE rel w/ early breast | One 2nd deg MALE rel w/ early breast | One 2nd deg rel w/ ovarian | One 2nd deg MALE rel w/ late breast | TWO 2nd deg FEMALE rel w/ late breast | One 2nd deg FEMALE rel w/ late breast | No 2nd deg rel w/ breast or ovarian |
|---|---|---|---|---|---|---|---|---|---|
| One 1st deg rel w/ early breast and ovarian | 2-046 H a,c,e,i,k | 2-047 H a,c,e,i,k | 2-048 H a,c,e,i,k | 2-049 H a,c,d,e,i,k | 2-050 H a,c,e,f,k | 2-051 H a,c,d,e,i,k | 2-052 H a,c,e,i,k | 2-053 H a,c,e,i,k | H a,c,e,f,k |
| One 1st deg rel w/ late breast and ovarian | 2-054 H a,c,e,i,k | 2-055 H a,c,i,k | 2-056 H a,c,e,i,k | 2-057 H a,c,d,e,i,k | 2-058 H a,c,f,k | 2-059 H a,c,d,i,k | 2-060 H a,c,i,k | 2-061 H a,c,i,k | H a,c,f,k |
| One 1st deg FEMALE rel w/ early breast | 2-062 H a,c,e,i,k | 2-063 H a,c,e,i,k | 2-064 H a,e,i,k | 2-065 H a,d,e,i,k | 2-066 H a,b,e,f,k | 2-067 H a,d,e,i,k | 2-068 H a,e,i,k | 2-069 H a,e,i,k | H a,e,f,k |
| One 1st deg MALE rel w/ early breast | 2-070 H a,c,d,e,i,k | 2-071 H a,c,d,e,i,k | 2-072 H a,d,e,i,k | 2-073 H a,d,e,i,k | 2-074 H a,b,d,e,f,k | 2-075 H a,d,e,i,k | 2-076 H a,d,e,i,k | 2-077 H a,d,e,i,k | H a,d,e,f,k |
| One 1st deg rel w/ ovarian | 2-078 H a,c,e,f,k | 2-079 H a,c,f,k | 2-080 H a,b,e,f,k | 2-081 H a,b,d,e,f,k | 2-082 H a,c,k | 2-083 H a,b,d,f,k | 2-084 H a,b,i,k | 2-085 H a,b,f,k | H a,G,k |
| One 1st deg MALE rel w/ late breast | 2-086 H a,c,d,e,i,k | 2-087 H a,c,d,i,k | 2-088 H a,d,e,i,k | 2-089 H a,d,e,i,k | 2-090 H a,b,d,f,k | 2-091 H a,d,i,k | 2-092 H a,d,i,k | 2-093 H a,d,i,k | H a,d,f,k |
| TWO 1st deg FEMALE rel w/ late breast | 2-094 H a,c,d,e,i,k | 2-095 H a,c,i,k | 2-096 H a,e,i,k | 2-097 H a,d,e,i,k | 2-098 H a,b,i,k | 2-099 H a,d,i,k | 2-100 H a,i,k | 2-101 H a,i,k | H a,f,k |
| One 1st deg FEMALE rel w/ late breast | 2-102 H a,c,e,i,k | 2-103 H a,c,i,k | 2-104 H a,e,i,k | 2-105 H a,d,e,i,k | 2-106 H a,b,f,k | 2-107 H a,d,i,k | 2-108 H a,i,k | 2-109 H a,i,k | H a,k |
| No 1st deg rel with breast or ovarian | H a,c,e,f,k | H a,c,f,k | H a,e,f,k | H a,d,e,f,k | H a,c,k | H a,d,f,k | H a,i,k | H a,f,k | H a,k |

FIG. 11

| For female user, personal history of both late-onset breast cancer and ovarian cancer at any age, and ... | | | | | | | | | |
|---|---|---|---|---|---|---|---|---|---|
| | One 2$^{nd}$ deg rel w/ early breast and ovarian | One 2$^{nd}$ deg rel w/ late breast and ovarian | One 2$^{nd}$ deg FEMALE rel w/ early breast | One 2$^{nd}$ deg MALE rel w/ early breast | One 2$^{nd}$ deg rel w/ ovarian | One 2$^{nd}$ deg MALE rel w/ late breast | TWO 2$^{nd}$ deg FEMALE rel w/ late breast | One 2$^{nd}$ deg FEMALE rel w/ late breast | No 2$^{nd}$ deg rel w/ breast or ovarian |
| One 2$^{nd}$ deg rel w/ early breast and ovarian | 2-110<br>H<br>a, c, e, i, k | 2-111<br>H<br>a, c, e, i, k | 2-112<br>H<br>a, c, e, i, k | 2-113<br>H<br>a, c, d, e, i, k | 2-114<br>H<br>a, c, e, f, k | 2-115<br>H<br>a, c, d, e, i, k | 2-116<br>H<br>a, c, e, i, k | 2-117<br>H<br>a, c, e, i, k | 2-118<br>H<br>a, c, e, f, k |
| One 2$^{nd}$ deg rel w/ late breast and ovarian | H<br>a, c, e, i, k | 2-119<br>H<br>a, c, i, k | 2-120<br>H<br>a, c, e, i, k | 2-121<br>H<br>a, c, d, e, i, k | 2-122<br>H<br>a, c, f, k | 2-123<br>H<br>a, c, d, i, k | 2-124<br>H<br>a, c, i, k | 2-125<br>H<br>a, c, i, k | 2-126<br>H<br>a, c, f, k |
| One 2$^{nd}$ deg FEMALE rel w/ early breast | H<br>a, c, e, i, k | H<br>a, c, e, i, k | 2-127<br>H<br>a, e, i, k | 2-128<br>H<br>a, d, e, i, k | 2-129<br>H<br>a, b, e, f, k | 2-130<br>H<br>a, d, e, i, k | 2-131<br>H<br>a, e, i, k | 2-132<br>H<br>a, e, i, k | 2-133<br>H<br>a, e, f, k |
| One 2$^{nd}$ deg MALE rel w/ early breast | H<br>a, c, d, e, i, k | H<br>a, c, d, e, i, k | H<br>a, d, e, i, k | 2-134<br>H<br>a, d, e, i, k | 2-135<br>H<br>a, b, d, e, f, k | 2-136<br>H<br>a, d, e, i, k | 2-137<br>H<br>a, d, e, i, k | 2-138<br>H<br>a, d, e, i, k | 2-139<br>H<br>a, d, e, f, k |
| One 2$^{nd}$ deg rel w/ ovarian | H<br>a, c, e, f, k | H<br>a, c, f, k | H<br>a, b, e, f, k | H<br>a, b, d, e, f, k | 2-140<br>H<br>a, c, k | 2-141<br>H<br>a, b, d, f, k | 2-142<br>H<br>a, b, i, k | 2-143<br>H<br>a, b, f, k | 2-144<br>H<br>a, c, k |
| One 2$^{nd}$ deg MALE rel w/ late breast | H<br>a, c, d, e, i, k | H<br>a, c, d, i, k | H<br>a, d, e, i, k | H<br>a, d, e, i, k | H<br>a, b, d, f, k | 2-145<br>H<br>a, d, i, k | 2-146<br>H<br>a, d, i, k | 2-147<br>H<br>a, d, i, k | 2-148<br>H<br>a, d, f, k |
| TWO 2$^{nd}$ deg FEMALE rel w/ late breast | H<br>a, c, e, i, k | H<br>a, c, i, k | H<br>a, e, i, k | H<br>a, d, e, i, k | H<br>a, b, i, k | H<br>a, d, i, k | 2-149<br>H<br>a, i, k | 2-150<br>H<br>a, i, k | 2-151<br>H<br>a, i, k |
| One 2$^{nd}$ deg FEMALE rel w/ late breast | H<br>a, c, e, i, k | H<br>a, c, i, k | H<br>a, e, i, k | H<br>a, d, e, i, k | H<br>a, b, f, k | H<br>a, d, i, k | H<br>a, i, k | 2-152<br>H<br>a, i, k | 2-153<br>H<br>a, f, k |
| No 2$^{nd}$ deg rel with breast or ovarian | H<br>a, c, e, f, k | H<br>a, c, f, k | H<br>a, e, f, k | H<br>a, d, e, f, k | H<br>a, c, k | H<br>a, d, f, k | H<br>a, i, k | H<br>a, f, k | 2-154<br>H<br>a, k |

FIG. 12

For female user, personal history of early-onset breast cancer and no history of ovarian cancer, and . . .
For male user, personal history of breast cancer at any age of onset, and . . .

|  | One 1st deg rel w/ early breast and ovarian | One 1st deg rel w/ late breast and ovarian | One 1st deg FEMALE rel w/ early breast | One 1st deg MALE rel w/ early breast | One 1st deg rel w/ ovarian | One 1st deg MALE rel w/ late breast | TWO 1st deg FEMALE rel w/ late breast | One 1st deg FEMALE rel w/ late breast | No 1st deg rel w/ breast or ovarian |
|---|---|---|---|---|---|---|---|---|---|
| One 1st deg rel w/ early breast and ovarian | 3-001 H a, c, e, i, k | 3-002 H a, c, e, i, k | 3-003 H a, e, i, k | 3-004 H a, d, e, i, k | 3-005 H a, c, e, f, k | 3-006 H a, d, e, i, k | 3-007 H a, e, i, k | 3-008 H a, e, i, k | 3-009 H a, e, f, k |
| One 1st deg rel w/ late breast and ovarian | H a, c, e, i, k | 3-010 H a, c, e, i, k | 3-011 H a, e, i, k | 3-012 H a, d, e, i, k | 3-013 H a, c, e, f, k | 3-014 H a, d, e, i, k | 3-015 H a, e, i, k | 3-016 H a, e, i, k | 3-017 H a, e, f, k |
| One 1st deg FEMALE rel w/ early breast | H a, e, i, k | H a, e, i, k | 3-018 H e, i, k | 3-019 H d, e, i, k | 3-020 H b, e, f, k | 3-021 H d, e, i, k | 3-022 H e, i, k | 3-023 H e, i, k | 3-024 H e, f, k |
| One 1st deg MALE rel w/ early breast | H a, d, e, i, k | H a, d, e, i, k | H d, e, i, k | 3-025 H d, e, i, k | 3-026 H b, d, e, f, k | 3-027 H d, e, i, k | 3-028 H d, e, i, k | 3-029 H d, e, i, k | 3-030 H d, e, f, k |
| One 1st deg rel w/ ovarian | H a, c, e, f, k | H a, c, e, f, k | H b, d, e, f, k | H b, d, e, f, k | 3-031 H b, c, e, k | 3-032 H b, d, e, f, k | 3-033 H b, e, i, k | 3-034 H b, e, i, k | 3-035 H b, e, k |
| One 1st deg MALE rel w/ late breast | H a, d, e, i, k | H a, d, e, i, k | H d, e, i, k | H d, e, i, k | H b, d, e, f, k | 3-036 H d, e, i, k | 3-037 H d, e, i, k | 3-038 H d, e, i, k | 3-039 H d, e, f, k |
| Two 1st deg FEMALE rel w/ late breast | H a, e, i, k | H a, e, i, k | H e, i, k | H d, e, i, k | H b, e, i, k | H d, e, i, k | 3-040 H e, i, k | 3-041 H e, i, k | 3-042 H e, i, k |
| One 1st deg FEMALE rel w/ late breast | H a, e, i, k | H a, e, i, k | H e, i, k | H d, e, i, k | H b, e, f, k | H d, e, i, k | H e, i, k | 3-043 H e, i, k | 3-044 H e, f, k |
| No 1st deg rel with breast or ovarian | H a, e, f, k | H a, e, f, k | H e, f, k | H d, e, f, k | H b, e, k | H d, e, f, k | H e, i, k | H e, f, k | 3-045 H e, k |

FIG. 13

For female user, personal history of early-onset breast cancer and no history of ovarian cancer, and ...
For male user, personal history of breast cancer at any age of onset, and ...

| | One 2nd deg rel w/ early breast and ovarian | One 2nd deg rel w/ late breast and ovarian | One 2nd deg FEMALE rel w/ early breast | One 2nd deg MALE rel w/ early breast | One 2nd deg rel w/ ovarian | One 2nd deg MALE rel w/ late breast | TWO 2nd deg FEMALE rel w/ late breast | One 2nd deg FEMALE rel w/ late breast | No 2nd deg rel w/ breast or ovarian |
|---|---|---|---|---|---|---|---|---|---|
| One 1st deg rel w/ early breast and ovarian | 3-046 H a, c, e, i, k | 3-047 H a, c, e, i, k | 3-048 H a, e, i, k | 3-049 H a, d, e, i, k | 3-050 H a, c, e, f, k | 3-051 H a, d, e, i, k | 3-052 H a, e, i, k | 3-053 H a, e, i, k | H a, e, f, k |
| One 1st deg rel w/ late breast and ovarian | 3-054 H a, c, e, i, k | 3-055 H a, c, e, i, k | 3-056 H a, e, i, k | 3-057 H a, d, e, i, k | 3-058 H a, c, e, f, k | 3-059 H a, d, e, i, k | 3-060 H a, e, i, k | 3-061 H a, e, i, k | H a, e, f, k |
| One 1st deg FEMALE rel w/ early breast | 3-062 H a, e, i, k | 3-063 H a, e, i, k | 3-064 H e, i, k | 3-065 H d, e, i, k | 3-066 H b, e, f, k | 3-067 H d, e, i, k | 3-068 H e, i, k | 3-069 H e, i, k | H e, f, k |
| One 1st deg MALE rel w/ early breast | 3-070 H a, d, e, i, k | 3-071 H a, d, e, i, k | 3-072 H d, e, i, k | 3-073 H d, e, i, k | 3-074 H b, d, e, f, k | 3-075 H d, e, i, k | 3-076 H d, e, i, k | 3-077 H d, e, i, k | H d, e, f, k |
| One 1st deg rel w/ ovarian | 3-078 H a, c, e, f, k | 3-079 H a, c, e, f, k | 3-080 H b, e, f, k | 3-081 H b, d, e, f, k | 3-082 H b, c, e, k | 3-083 H b, d, e, f, k | 3-084 H b, e, i, k | 3-085 H b, e, f, k | H b, e, k |
| One 1st deg MALE rel w/ late breast | 3-086 H a, d, e, i, k | 3-087 H a, d, e, i, k | 3-088 H d, e, i, k | 3-089 H d, e, i, k | 3-090 H b, d, e, f, k | 3-091 H d, e, i, k | 3-092 H d, e, i, k | 3-093 H d, e, i, k | H d, e, f, k |
| TWO 1st deg FEMALE rel w/ late breast | 3-094 H a, e, i, k | 3-095 H a, e, i, k | 3-096 H e, i, k | 3-097 H d, e, i, k | 3-098 H b, e, i, k | 3-099 H d, e, i, k | 3-100 H e, i, k | 1-101 H e, i, k | H e, i, k |
| One 1st deg FEMALE rel w/ late breast | 3-102 H a, e, i, k | 3-103 H a, e, i, k | 3-104 H e, i, k | 3-105 H d, e, i, k | 3-106 H b, e, f, k | 3-107 H d, e, i, k | 3-108 H e, i, k | 3-109 H e, i, k | H e, i, k |
| No 1st deg rel with breast or ovarian | H a, e, i, k | H a, e, f, k | H e, f, k | H d, e, f, k | H b, e, g, k | H d, e, f, k | H e, f, k | H e, f, k | H e, k |

FIG. 14

For female user, personal history of early-onset breast cancer and no history of ovarian cancer, and ...
For male user, personal history of breast cancer at any age of onset, and ...

| | One 2nd deg rel w/ early breast and ovarian | One 2nd deg rel w/ late breast and ovarian | One 2nd deg FEMALE rel w/ early breast | One 2nd deg MALE rel w/ early breast | One 2nd deg rel w/ ovarian | One 2nd deg MALE rel w/ late breast | TWO 2nd deg FEMALE rel w/ late breast | One 2nd deg FEMALE rel w/ late breast | No 2nd deg rel w/ breast or ovarian |
|---|---|---|---|---|---|---|---|---|---|
| One 2nd deg rel w/ early breast and ovarian | 3-110<br>H<br>a, c, e, i, k | 3-111<br>H<br>a, c, e, i, k | 3-112<br>H<br>a, e, i, k | 3-113<br>H<br>a, d, e, i, k | 3-114<br>H<br>a, c, e, f, k | 3-115<br>H<br>a, d, e, i, k | 3-116<br>H<br>a, e, i, k | 3-117<br>H<br>a, e, i, k | 3-118<br>H<br>a, e, f, k |
| One 2nd deg rel w/ late breast and ovarian | H<br>a, c, e, i, k | 3-119<br>H<br>a, c, e, i, k | 3-120<br>H<br>a, e, i, k | 3-121<br>H<br>a, d, e, i, k | 3-122<br>H<br>a, c, e, f, k | 3-123<br>H<br>a, d, e, i, k | 3-124<br>H<br>a, e, i, k | 3-125<br>H<br>a, e, i, k | 3-126<br>H<br>a, e, f, k |
| One 2nd deg FEMALE rel w/ early breast | H<br>a, e, i, k | H<br>a, e, i, k | 3-127<br>H<br>e, i, k | 3-128<br>H<br>d, e, i, k | 3-129<br>H<br>b, e, f, k | 3-130<br>H<br>d, e, i, k | 3-131<br>H<br>e, i, k | 3-132<br>H<br>e, i, k | 3-133<br>H<br>e, i, k |
| One 2nd deg MALE rel w/ early breast | H<br>a, d, e, i, k | H<br>a, d, e, i, k | H<br>d, e, i, k | 3-134<br>H<br>d, e, i, k | 3-135<br>H<br>b, d, e, f, k | 3-136<br>H<br>d, e, i, k | 3-137<br>H<br>d, e, i, k | 3-138<br>H<br>d, e, i, k | 3-139<br>H<br>d, e, f, k |
| One 2nd deg rel w/ ovarian | H<br>a, c, e, f, k | H<br>a, c, e, f, k | H<br>b, e, f, k | H<br>b, d, e, f, k | 3-140<br>H<br>b, d, e, f, k | 3-141<br>H<br>b, d, e, f, k | 3-142<br>H<br>b, e, i, k | 3-143<br>H<br>b, e, f, k | 3-144<br>H<br>b, e, k |
| One 2nd deg MALE rel w/ late breast | H<br>a, d, e, i, k | H<br>a, d, e, i, k | H<br>d, e, i, k | H<br>d, e, i, k | H<br>b, d, e, f, k | 3-145<br>H<br>d, e, i, k | 3-146<br>H<br>d, e, i, k | 3-147<br>H<br>d, e, i, k | 3-148<br>H<br>d, e, f, k |
| TWO 2nd deg FEMALE rel w/ late breast | H<br>a, e, i, k | H<br>a, e, i, k | H<br>e, i, k | H<br>d, e, i, k | H<br>b, e, i, k | H<br>d, e, i, k | 3-149<br>H<br>e, i, k | 3-150<br>H<br>e, i, k | 3-151<br>H<br>e, i, k |
| One 2nd deg FEMALE rel w/ late breast | H<br>a, e, i, k | H<br>a, e, i, k | H<br>e, i, k | H<br>d, e, i, k | H<br>b, e, f, k | H<br>d, e, i, k | H<br>e, i, k | 3-152<br>H<br>e, i, k | 3-153<br>H<br>e, i, k |
| No 2nd deg rel with breast or ovarian | H<br>a, e, f, k | H<br>a, e, f, k | H<br>e, f, k | H<br>d, e, f, k | H<br>b, e, f, k | H<br>d, e, f, k | H<br>e, i, k | H<br>e, f, k | 3-154<br>H<br>e, k |

For female user, personal history of late-onset breast cancer and no history of ovarian cancer, and ...

| | One 1st deg rel w/ early breast and ovarian | One 1st deg rel w/ late breast and ovarian | One 1st deg FEMALE rel w/ early breast | One 1st deg MALE rel w/ early breast | One 1st deg rel w/ ovarian | One 1st deg MALE rel w/ late breast | TWO 1st deg FEMALE rel w/ late breast | One 1st deg FEMALE rel w/ late breast | No 1st deg rel w/ breast or ovarian |
|---|---|---|---|---|---|---|---|---|---|
| One 1st deg rel w/ early breast and ovarian | 4-001 H a,c,e,i | 4-002 H a,c,e,i | 4-003 H a,e,i | 4-004 H a,d,e,i | 4-005 H a,c,e,f | 4-006 H a,d,e,i | 4-007 H a,e,i | 4-008 H a,e,i | 4-009 H a,e,f |
| One 1st deg rel w/ late breast and ovarian | H a,c,e,i | 4-010 H a,c,i | 4-011 H a,e,i | 4-012 H a,d,e,i | 4-013 H a,c,f | 4-014 H a,d,i | 4-015 H a,i | 4-016 H a,i | 4-017 H a,f |
| One 1st deg FEMALE rel w/ early breast | H a,e,i | H a,e,i | 4-018 H - | 4-019 H d,e,i | 4-020 H b,e,f | 4-021 H d,e,i | 4-022 H e,i | 4-023 H e,i | 4-024 H e,f |
| One 1st deg MALE rel w/ early breast | H a,d,e,i | H a,d,e,i | H e,i | 4-025 H d,e,i | 4-026 H b,d,e,f | 4-027 H d,e,i | 4-028 H d,e,i | 4-029 H d,e,i | 4-030 H d,e,f |
| One 1st deg rel w/ ovarian | H a,c,e,f | H a,c,f | H b,e,f | H b,d,e,f | 4-031 H b,c | 4-032 H b,d,f | 4-033 H b,i | 4-034 H b,f | 4-035 H b |
| One 1st deg MALE rel w/ late breast | H a,d,e,i | H a,d,i | H d,e,i | H d,e,i | H b,d,f | 4-036 H d,i | 4-037 H d,i | 4-038 H d,i | 4-039 H d,f |
| Two 1st deg FEMALE rel w/ late breast | H a,e,i | H a,i | H e,i | H d,e,i | H b,i | H d,i | 4-040 H - | 4-041 H - | 4-042 H - |
| One 1st deg FEMALE rel w/ late breast | H a,e,i | H a,i | H e,i | H d,e,i | H b,f | H d,i | H - | 4-043 H - | 4-044 H f |
| No 1st deg rel with breast or ovarian | H a,e,f | H a,f | H e,f | H d,e,f | H b | H d,f | H - | H f | 4-045 A |

For female user, personal history of late-onset breast cancer and no history of ovarian cancer, and ...

| | One 2nd deg rel w/ early breast and ovarian | One 2nd deg rel w/ late breast and ovarian | One 2nd deg FEMALE rel w/ early breast | One 2nd deg MALE rel w/ early breast | One 2nd deg rel w/ ovarian | One 2nd deg MALE rel w/ late breast | TWO 2nd deg FEMALE rel w/ late breast | One 2nd deg FEMALE rel w/ late breast | No 2nd deg rel w/ breast or ovarian |
|---|---|---|---|---|---|---|---|---|---|
| One 1st deg rel w/ early breast and ovarian | 4-046 H a, c, e, i | 4-047 H a, c, e, i | 4-048 H a, e, i | 4-049 H a, d, e, i | 4-050 H a, c, e, f | 4-051 H a, d, e, i | 4-052 H a, e, i | 4-053 H a, e, i | H a, e, f |
| One 1st deg rel w/ late breast and ovarian | 4-054 H a, c, e, i | 4-055 H a, c, i | 4-056 H a, e, i | 4-057 H a, d, e, i | 4-058 H a, c, f | 4-059 H a, d, i | 4-060 H a, i | 4-061 H a, i | H a, f |
| One 1st deg FEMALE rel w/ early breast | 4-062 H a, e, i | 4-063 H a, e, i | 4-064 H e, i | 4-065 H d, e, i | 4-066 H b, e, f | 4-067 H d, e, i | 4-068 H e, i | 4-069 H e, i | H e, f |
| One 1st deg MALE rel w/ early breast | 4-070 H a, d, e, i | 4-071 H a, d, e, i | 4-072 H d, e, i | 4-073 H d, e, i | 4-074 H b, d, e, f | 4-075 H d, e, i | 4-076 H d, e, i | 4-077 H d, e, i | H d, e, f |
| One 1st deg rel w/ ovarian | 4-078 H a, c, e, f | 4-079 H a, c, f | 4-080 H b, e, f | 4-081 H b, d, e, f | 4-082 H b, c | 4-083 H b, d, f | 4-084 H b, i | 4-085 H b, f | H b |
| One 1st deg MALE rel w/ late breast | 4-086 H a, d, e, i | 4-087 H a, d, i | 4-088 H d, e, i | 4-089 H d, e, i | 4-090 H b, d, f | 4-091 H d, i | 4-092 H d, i | 4-093 H d, i | H d, f |
| TWO 1st deg FEMALE rel w/ late breast | 4-094 H a, e, i | 4-095 H a, i | 4-096 H e, i | 4-097 H d, e, i | 4-098 H b, i | 4-099 H d, i | 4-100 H i | 4-101 H i | H i |
| One 1st deg FEMALE rel w/ late breast | 4-102 H a, e, i | 4-103 H a, i | 4-104 H e, i | 4-105 H d, e, i | 4-106 H b, f | 4-107 H d, i | 4-108 H i | 4-109 H i | H f |
| No 1st deg rel with breast or ovarian | H a, e, f | H a, f | H e, f | H d, e, f | H b | H d, f | H i | M f | A |

FIG. 17

For female user, personal history of late-onset breast cancer and no history of ovarian cancer, and ...

| | One 2nd deg rel w/ early breast and ovarian | One 2nd deg rel w/ late breast and ovarian | One 2nd deg FEMALE rel w/ early breast | One 2nd deg MALE rel w/ early breast | One 2nd deg rel w/ ovarian | One 2nd deg MALE rel w/ late breast | TWO 2nd deg FEMALE rel w/ late breast | One 2nd deg FEMALE rel w/ late breast | No 2nd deg rel w/ breast or ovarian |
|---|---|---|---|---|---|---|---|---|---|
| One 2nd deg rel w/ early breast and ovarian | 4-110<br>H<br>a, c, e, f | 4-111<br>H<br>a, c, e, f | 4-112<br>H<br>a, e, f | 4-113<br>H<br>a, d, e, f | 4-114<br>H<br>a, c, e, f | 4-115<br>H<br>a, d, e, f | 4-116<br>H<br>a, e, f | 4-117<br>H<br>a, e, f | 4-118<br>H<br>a, e, f |
| One 2nd deg rel w/ late breast and ovarian | H<br>a, c, e, f | 4-119<br>H<br>a, c, f | 4-120<br>H<br>a, e, f | 4-121<br>H<br>a, d, e, f | 4-122<br>H<br>a, c, f | 4-123<br>H<br>a, d, f | 4-124<br>H<br>a, f | 4-125<br>H<br>a, f | 4-126<br>H<br>a, f |
| One 2nd deg FEMALE rel w/ early breast | H<br>a, e, f | H<br>a, e, f | 4-127<br>H<br>e, f | 4-128<br>H<br>d, e, f | 4-129<br>H<br>b, e, f | 4-130<br>H<br>d, e, f | 4-131<br>H<br>e, f | 4-132<br>H<br>e, f | 4-133<br>H<br>e, f |
| One 2nd deg MALE rel w/ early breast | H<br>a, d, e, f | H<br>a, d, e, f | H<br>d, e, f | 4-134<br>H<br>d, e, f | 4-135<br>H<br>b, d, e, f | 4-136<br>H<br>d, e, f | 4-137<br>H<br>d, e, f | 4-138<br>H<br>d, e, f | 4-139<br>H<br>d, e, f |
| One 2nd deg rel w/ ovarian | H<br>a, c, f | H<br>a, c, f | H<br>b, e, f | H<br>b, d, e, f | 4-140<br>H<br>b, c | 4-141<br>H<br>b, d, f | 4-142<br>H<br>b, f | 4-143<br>H<br>b, f | 4-144<br>H<br>b |
| One 2nd deg MALE rel w/ late breast | H<br>a, d, e, f | H<br>a, d, f | H<br>d, e, f | H<br>d, e, f | H<br>b, d, f | 4-145<br>H<br>d, f | 4-146<br>H<br>d, f | 4-147<br>H<br>d, f | 4-148<br>H<br>d, f |
| TWO 2nd deg FEMALE rel w/ late breast | H<br>a, e, f | H<br>a, f | H<br>e, f | H<br>d, e, f | H<br>b, f | H<br>d, f | 4-149<br>H<br>f | 4-150<br>H<br>f | 4-151<br>H<br>f |
| One 2nd deg FEMALE rel w/ late breast | H<br>a, e, f | H<br>a, f | H<br>e, f | H<br>d, e, f | H<br>b, f | H<br>d, f | H<br>f | 4-152<br>H<br>i | 4-153<br>M<br>f |
| No 2nd deg rel with breast or ovarian | H<br>a, e, f | H<br>a, f | H<br>e, f | H<br>d, e, f | H<br>b | H<br>d, f | H<br>f | M<br>f | 4-154<br>A |

FIG. 18

For female user, personal history of ovarian cancer at any age of onset and no history of breast cancer, and ...

| | One 1st deg rel w/ early breast and ovarian | One 1st deg rel w/ late breast and ovarian | One 1st deg FEMALE rel w/ early breast | One 1st deg MALE rel w/ early breast | One 1st deg rel w/ ovarian | One 1st deg MALE rel w/ late breast | TWO 1st deg FEMALE rel w/ late breast | One 1st deg FEMALE rel w/ late breast | No 1st deg rel w/ breast or ovarian |
|---|---|---|---|---|---|---|---|---|---|
| One 1st deg rel w/ early breast and ovarian | 5-001 H a, c, e, f | 5-002 H a, c, e, f | 5-003 H a, c, e, f | 5-004 H a, c, d, e, f | 5-005 H a, c, e, f | 5-006 H a, c, d, e, f | 5-007 H a, c, e, i | 5-008 H a, c, e, f | 5-009 H a, c, e |
| One 1st deg rel w/ late breast and ovarian | H a, c, e, f | 5-010 H a, c, f | 5-011 H a, c, e, f | 5-012 H a, c, d, e, f | 5-013 H a, c | 5-014 H a, c, d | 5-015 H a, c, i | 5-016 H a, c, f | 5-017 H a, c |
| One 1st deg FEMALE rel w/ early breast | H a, c, e, f | H a, c, e, f | 5-018 H b, e, f | 5-019 H b, d, e, f | 5-020 H b, c, e | 5-021 H b, d, e, f | 5-022 H b, e, i | 5-023 H b, e, f | 5-024 H b, e |
| One 1st deg MALE rel w/ early breast | H a, c, d, e, f | H a, c, d, e, f | H b, d, e, f | 5-025 H b, d, e, f | 5-026 H b, c, d, e | 5-027 H b, d, e, f | 5-028 H b, d, e, i | 5-029 H b, d, e, f | 5-030 H b, d, e |
| One 1st deg rel w/ ovarian | H a, c, e | H a, c | H b, c, e | H b, c, d, e | 5-031 H c | 5-032 H b, c, d | 5-033 H b, c, f | 5-034 H b, c | 5-035 H c |
| One 1st deg MALE rel w/ late breast | H a, c, d, e, f | H a, c, d | H b, d, e, f | H b, d, e, f | H b, c, d | 5-036 H b, d, f | 5-037 H b, d, i | 5-038 H b, d, f | 5-039 H b, d |
| Two 1st deg FEMALE rel w/ late breast | H a, c, e, i | H a, c, i | H b, e, i | H b, d, e, i | H b, c, f | H b, d, i | 5-040 H b, i | 5-041 H b, i | 5-042 H b, f |
| One 1st deg FEMALE rel w/ late breast | H a, c, e, f | H a, c, f | H b, e, f | H b, d, e, f | H b, c | H b, d, f | H b, i | 5-043 H b, f | 5-044 H b |
| No 1st deg rel with breast or ovarian | H a, c, e | H a, c | H b, e | H b, d, e | H c | H b, d | H b, f | H b | 5-045 A if AJ, H k |

FIG. 19

For female user, personal history of ovarian cancer at any age of onset and no history of breast cancer, and . . .

| | One 2nd deg rel w/ early breast and ovarian | One 2nd deg rel w/ late breast and ovarian | One 2nd deg FEMALE rel w/ early breast | One 2nd deg MALE rel w/ early breast | One 2nd deg rel w/ ovarian | One 2nd deg MALE rel w/ late breast | TWO 2nd deg FEMALE rel w/ late breast | One 2nd deg FEMALE rel w/ late breast | No 2nd deg rel w/ breast or ovarian |
|---|---|---|---|---|---|---|---|---|---|
| One 1st deg rel w/ early breast and ovarian | 5-046 H a, c, e, f | 5-047 H a, c, e, f | 5-048 H a, c, e, f | 5-049 H a, c, d, e, f | 5-050 H a, c, e | 5-051 H a, c, d, e, f | 5-052 H a, c, e, i | 5-053 H a, c, e, f | H a, c, e |
| One 1st deg rel w/ late breast and ovarian | 5-054 H a, c, e, f | 5-055 H a, c, f | 5-056 H a, c, e, f | 5-057 H a, c, d, e, f | 5-058 H a, c | 5-059 H a, c, d | 5-060 H a, c, i | 5-061 H a, c, f | H a, c |
| One 1st deg FEMALE rel w/ early breast | 5-062 H a, c, e, f | 5-063 H a, c, e, f | 5-064 H b, e, f | 5-065 H b, d, e, f | 5-066 H b, c, e | 5-067 H b, d, e, f | 5-068 H b, e, i | 5-069 H b, e, f | H b, e |
| One 1st deg MALE rel w/ early breast | 5-070 H a, c, d, e, f | 5-071 H a, c, d, e, f | 5-072 H b, d, e, f | 5-073 H b, d, e, f | 5-074 H b, c, d, e | 5-075 H b, d, e, f | 5-076 H b, d, e, i | 5-077 H b, d, e, f | H b, d, e |
| One 1st deg rel w/ ovarian | 5-078 H a, c, e | 5-079 H a, c | 5-080 H b, c, e | 5-081 H b, c, d, e | 5-082 H c | 5-083 H b, c, d | 5-084 H b, c, f | 5-085 H b, c | H c |
| One 1st deg MALE rel w/ late breast | 5-086 H a, c, d, e, f | 5-087 H a, c, d | 5-088 H b, d, e, f | 5-089 H b, c, d, e, f | 5-090 H b, c, d | 5-091 H b, d, f | 5-092 H b, d, i | 5-093 H b, d, f | H b, d |
| TWO 1st deg FEMALE rel w/ late breast | 5-094 H | 5-095 H | 5-096 H b, e, i | 5-097 H b, d, e, i | 5-098 H b, c, f | 5-099 H b, d, i | 5-100 H b, i | 5-101 H b, i | H b, f |
| One 1st deg FEMALE rel w/ late breast | 5-102 H a, c, e, f | 5-103 H a, c, f | 5-104 H b, e, f | 5-105 H b, d, e, f | 5-106 H b, c | 5-107 H b, d, f | 5-108 H b, i | 5-109 H b, f | H b |
| No 1st deg rel with breast or ovarian | H a, c, e | H a, c | H b, e | H b, d, e | H c | H b, d | H b, f | M b if AJ, H b | A if AJ, H k |

For female user, personal history of ovarian cancer at any age of onset and no history of breast cancer, and ...

| | One 2nd deg rel w/ early breast and ovarian | One 2nd deg rel w/ late breast and ovarian | One 2nd deg FEMALE rel w/ early breast | One 2nd deg MALE rel w/ early breast | One 2nd deg rel w/ ovarian | One 2nd deg MALE rel w/ late breast | TWO 2nd deg FEMALE rel w/ late breast | One 2nd deg FEMALE rel w/ late breast | No 2nd deg rel w/ breast or ovarian |
|---|---|---|---|---|---|---|---|---|---|
| One 2nd deg rel w/ early breast and ovarian | 5-110 H a, c, e, f | 5-111 H a, c, e, f | 5-112 H a, c, e, f | 5-113 H a, c, d, e, f | 5-114 H a, c, e | 5-115 H a, c, d, e, f | 5-116 H a, c, e, i | 5-117 H a, c, e, f | 5-118 H a, c, e |
| One 2nd deg rel w/ late breast and ovarian | H a, c, e, f | 5-119 H a, c, f | 5-120 H a, c, e, f | 5-121 H a, c, d, e, f | 5-122 H a, c | 5-123 H a, c, d | 5-124 H a, c, i | 5-125 H a, c, f | 5-126 H a, c |
| One 2nd deg FEMALE rel w/ early breast | H a, c, e, f | H a, c, e, f | 5-127 H b, e, f | 5-128 H b, d, e, f | 5-129 H b, c, e | 5-130 H b, d, e, f | 5-131 H b, e, i | 5-132 H b, e, f | 5-133 H b, e |
| One 2nd deg MALE rel w/ early breast | H a, c, d, e, f | H a, c, e, f | H b, d, e, f | 5-134 H b, d, e, f | 5-135 H b, c, d, e | 5-136 H b, d, e, f | 5-137 H b, d, e, i | 5-138 H b, d, e, f | 5-139 H b, d, e |
| One 2nd deg rel w/ ovarian | H a, c, e | H a, c | H b, c, e | H b, c, d, e | H c | H b, c, d | 5-142 H b, c, f | 5-143 H b, c | 5-144 H c |
| One 2nd deg MALE rel w/ late breast | H a, c, d, e, f | H a, c, d | H b, d, e, f | H b, d, e, f | H b, c, d | 5-145 H b, d, f | 5-146 H b, d, i | 5-147 H b, d, f | 5-148 H b, d |
| TWO 2nd deg FEMALE rel w/ late breast | H a, c, e, i | H a, c, i | H b, e, i | H b, d, e, i | H b, c, f | H b, d, i | 5-149 H b, i | 5-150 H b, i | 5-151 H b, f |
| One 2nd deg FEMALE rel w/ late breast | H a, c, e, f | H a, c, f | H b, e, f | H b, d, e, f | H b, c | H b, d, f | H b, i | 5-152 H b, f | 5-153 M b if AJ, H b |
| No 2nd deg rel with breast or ovarian | H a, c, e | H a, c | H b, e | H b, d, e | H c | H b, d | H b, f | M, b if AJ, H b | 5-154 A if AJ, H k |

For female or male user, no personal history of breast cancer and no personal history of ovarian cancer, and . . .

|  | One 1st deg rel w/ early breast ca and ovarian | One 1st deg rel w/ late breast ca and ovarian | One 1st deg FEMALE rel w/ early breast ca | One 1st deg MALE rel w/ early breast ca | One 1st deg rel w/ ovarian | One 1st deg MALE rel w/ late breast | TWO 1st deg FEMALE rel w/ late breast | One 1st deg FEMALE rel w/ late breast | No 1st deg rel w/ breast |
|---|---|---|---|---|---|---|---|---|---|
| One 1st deg rel w/ early breast and ovarian | 6-001 H a, c, e, f | 6-002 H a, c, e, f | 6-003 H a, e, f | 6-004 H a, d, e, f | 6-005 H a, c, e | 6-006 H a, d, e, f | 6-007 H a, e, i | 6-008 H a, e, f | 6-009 H a, e |
| One 1st deg rel w/ late breast and ovarian | H a, c, e, f | 6-010 H a, c, f | 6-011 H a, e, f | 6-012 H a, d, e, f | 6-013 H a, c | 6-014 H a, d, f | 6-015 H a, i | 6-016 H a, f | 6-017 H a |
| One 1st deg FEMALE rel w/ early breast | H a, e, f | H a, e, f | 6-018 H e, f | 6-019 H d, e, f | 6-020 H b, e | 6-021 H d, e, f | 6-022 H e, i | 6-023 H e, f | 6-024 H e |
| One 1st deg MALE rel w/ early breast | H a, d, e, f | H a, d, e, f | H d, e, f | 6-025 H d, e, f | 6-026 H b, d, e | 6-027 H d, e, f | 6-028 H d, e, i | 6-029 H d, e, f | 6-030 H d, e |
| One 1st deg rel w/ ovarian | H a, c, e | H a, c | H b, e | H b, d, e | 6-031 H c | 6-032 H b, d | 6-033 H b, f | 6-034 M, b if AJ, H b | 6-035 A if AJ, H h |
| One 1st deg MALE rel w/ late breast | H a, d, e, f | H a, d, f | H d, e, f | H d, e, f | H b, d | 6-036 H d, f | 6-037 H d, i | 6-038 H d, f | 6-039 M, d if AJ, H d |
| Two 1st deg FEMALE rel w/ late breast | H a, e, f | H a, f | H e, f | H d, e, f | H b, f | H d, f | 6-040 H i | 6-041 H i | 6-042 H f |
| One 1st deg FEMALE rel w/ late breast | H a, e, f | H a, f | H e, f | H d, e, f | M, b if AJ, H b | H d, f | H f | 6-043 H f | 6-044 M g |
| No 1st deg rel with breast or ovarian | H a, e | H a | H e | H d, e | A if AJ, H h |  |  | M g | 6-045 A |

FIG. 22

| | One 2nd deg rel w/ early breast and ovarian | One 2nd deg rel w/ late breast and ovarian | One 2nd deg FEMALE rel w/ early breast | One 2nd deg MALE rel w/ early breast | One 2nd deg rel w/ ovarian | One 2nd deg MALE rel w/ late breast | TWO 2nd deg FEMALE rel w/ late breast | One 2nd deg FEMALE rel w/ late breast | No 2nd deg rel w/ breast or ovarian |
|---|---|---|---|---|---|---|---|---|---|
| One 1st deg rel w/ early breast and ovarian | 6-046 H a, c, e, f | 6-047 H a, c, e, f | 6-048 H a, e, f | 6-049 H a, d, e, f | 6-050 H a, c, e | 6-051 H a, d, e, f | 6-052 H a, e, i | 6-053 H a, e, f | H a, e |
| One 1st deg rel w/ late breast and ovarian | 6-054 H a, c, e, f | 6-055 H a, c, f | 6-056 H a, e, f | 6-057 H a, d, e, f | 6-058 H a, c | 6-059 H a, d, f | 6-060 H a, i | 6-061 H a, f | H a |
| One 1st deg FEMALE rel w/ early breast | 6-062 H a, e, f | 6-063 H a, e, f | 6-064 H e, f | 6-065 H d, e, f | 6-066 H b, e | 6-067 H d, e, f | 6-068 H e, i | 6-069 H e, f | H e |
| One 1st deg MALE rel w/ early breast | 6-070 H a, d, e, f | 6-071 H a, d, e, f | 6-072 H d, e, f | 6-073 H d, e, f | 6-074 H b, d, e | 6-075 H d, e, f | 6-076 H d, e, i | 6-077 H d, e, f | H d, e |
| One 1st deg rel w/ ovarian | 6-078 H a, c, e | 6-079 H a, c | 6-080 H b, e | 6-081 H b, d, e | 6-082 H c | 6-083 H b, d | 6-084 H b, f | 6-085 M, b if AJ, H b | A if AJ, H h |
| One 1st deg MALE rel w/ late breast | 6-086 H a, d, e, f | 6-087 H a, d, f | 6-088 H d, e, f | 6-089 H d, e, f | 6-090 H b, d | 6-091 H d, f | 6-092 H f | 6-093 H d, f | M, d if AJ, H d |
| TWO 1st deg FEMALE rel w/ late breast | 6-094 H a, e, i | 6-095 H a, i | 6-096 H e, i | 6-097 H d, e, i | 6-098 H b, f | 6-099 H d, i | 6-100 H i | 6-101 H i | H f |
| One 1st deg FEMALE rel w/ late breast | 6-102 H a, e, f | 6-103 H a, f | 6-104 M, e, f if pat or AJ, H e, f | 6-105 M, b if AJ, H b | 6-106 M, b if AJ, H b | 6-107 H d, f | 6-108 H i | 6-109 M f | M g |
| No 1st deg rel with breast or ovarian | H a, e | H a | A if pat or AJ, M e | A, if pat or AJ, M d, e | A if AJ, M h | A if AJ, M d | M f | A | A |

FIG. 23

For female or male user, no personal history of breast cancer and no personal history of ovarian cancer, and ...

| | One 2nd deg rel w/ early breast and ovarian | One 2nd deg rel w/ late breast and ovarian | One 2nd deg FEMALE rel w/ early breast | One 2nd deg MALE rel w/ early breast | One 2nd deg rel w/ ovarian | One 2nd deg MALE rel w/ late breast | TWO 2nd deg FEMALE rel w/ late breast | One 2nd deg FEMALE rel w/ late breast | No 2nd deg rel w/ breast or ovarian |
|---|---|---|---|---|---|---|---|---|---|
| One 2nd deg rel w/ early breast and ovarian | 6-110<br>H<br>a, c, e, f | 6-111<br>H<br>a, c, f | 6-112<br>H<br>a, e, f | 6-113<br>H<br>a, d, e, f | 6-114<br>H<br>a, c, e | 6-115<br>H<br>a, d, e, f | 6-116<br>H<br>a, e, i | 6-117<br>H<br>a, e, f | 6-118<br>H<br>a, e |
| One 2nd deg rel w/ late breast and ovarian | H<br>a, c, e, f | 6-119<br>H<br>a, c, f | 6-120<br>H<br>a, e, f | 6-121<br>H<br>a, d, e, f | 6-122<br>H<br>a, c | 6-123<br>H<br>a, d, f | 6-124<br>H<br>a, i | 6-125<br>H<br>a, f | 6-126<br>H<br>a |
| One 2nd deg FEMALE rel w/ early breast | H<br>a, d, e, f | H<br>a, e, f | 6-127<br>H<br>e, f | 6-128<br>H<br>d, e, f | 6-129<br>H<br>b, e | 6-130<br>H<br>d, e, f | 6-131<br>H<br>e, i | 6-132<br>H<br>e, f | 6-133<br>A<br>if pat or AJ, M<br>e |
| One 2nd deg MALE rel w/ early breast | H<br>a, d, e, f | H<br>a, d, e, f | H<br>d, e, f | 6-134<br>H<br>d, e, f | 6-135<br>H<br>b, d, e | 6-136<br>H<br>d, e, f | 6-137<br>H<br>d, e, i | 6-138<br>H<br>d, e, f | 6-139<br>A<br>if pat or AJ, M<br>d,e |
| One 2nd deg rel w/ ovarian | H<br>a, c, e | H<br>a, c | H<br>b, e | H<br>b, d, e | 6-140<br>H<br>c | 6-141<br>H<br>b, d | 6-142<br>H<br>b, f | 6-143<br>H<br>b | 6-144<br>A<br>if AJ, M<br>h |
| One 2nd deg MALE rel w/ late breast | H<br>a, d, e, f | H<br>a, d, f | H<br>d, e, f | H<br>d, e, f | H<br>b, d | 6-145<br>H<br>d, f | 6-146<br>H<br>d, i | 6-147<br>H<br>d, f | 6-148<br>A, if AJ, M<br>d |
| TWO 2nd deg FEMALE rel w/ late breast | H<br>a, e, f | H<br>a, f | H<br>e, f | H<br>d, e, f | H<br>b, f | H<br>d, f | 6-149<br>H<br>i | 6-150<br>H<br>i | 6-151<br>M<br>f |
| One 2nd deg FEMALE rel w/ late breast | H<br>a, e, f | H<br>a, f | H<br>e, f | H<br>d, e, f | H<br>b | H<br>d, f | H<br>i | 6-152<br>M<br>f | 6-153<br>A |
| No 2nd deg rel w/ breast or ovarian | H<br>a, e | H<br>a | A<br>if pat or AJ, M<br>e | A<br>if pat or AJ, M<br>d,e | A<br>if AJ, M<br>h | A<br>if AJ, M<br>d | M<br>f | A | 6-154<br>A |

FIG. 24

METHOD AND APPARATUS FOR DETERMINING FAMILIAL RISK OF DISEASE

This patent application claims the benefit of the earlier filing date of U.S. provisional application Ser. No. 60/650,076 entitled "Familial Risk Analysis for Determining a Disease Prevention Plan", filed Feb. 3, 2005.

FIELD

The field relates to preventative medicine and risk analysis of disease.

BACKGROUND

Determining risk factors for a disease can be helpful in managing a disease, and for assessing an individual's overall risk for a disease and in creating a plan to modify an individual's risk of developing a disease. Medical providers are under increasing pressure from governments, medical specialty organizations, managed care, and patients to practice preventative medicine. Similarly, health organizations and insurance companies are beginning to recognize that risk analysis of disease and preventative medicine can be a cost effective strategy for providing care. Medical screening and prevention guidelines for many chronic disorders have been developed by governmental and medical organizations to facilitate risk analysis of disease and preventive medicine practice. However, such guidelines can be slow to be adopted, sometimes poorly understood, counter to historical practice, and can be perceived as cumbersome, difficult to use, not readily accessible, or confusing by both medical providers and patients. Similarly, the guidelines do not incorporate comprehensive personalized family health history information to determine a patient-specific or personalized risk of disease and disease prevention plan. Accordingly, there remains a need to better assess disease risk and communicate risk to patients. In addition, clinical trials and epidemiologic investigations of risk factors for disease often fail to adequately assess the family history as a risk factor, often using limited definitions of family history. Improved assessment of familial risk in these investigations could help in elucidating the role of family history as a disease risk factor, and the potential role of genes in the development or natural history of disease.

SUMMARY

Personal and family health history information can be used to assess the familial risk of diseases and to determine disease management options and early detection and prevention strategies. For example, information can be collected about the disease history of a person and the person's first- and second-degree relatives (e.g., mother, father, children, siblings, grandparents, aunts and uncles) and then analyzed to determine the familial risk for one or more diseases (e.g., coronary heart disease, stroke, type 2 diabetes, and colorectal, breast, and ovarian cancer). Assessed familial risk of disease can then be used to stratify a clinical or research population into different levels of familial risk, and to determine recommendations for disease management, prevention and screening that are specific to the familial risk level.

The techniques described herein can be applied to any number of diseases in medical and non-medical settings where determining the familial risk of disease is desired.

Additional features and advantages of the technologies described herein will be made apparent from the following detailed description of illustrated embodiments, which proceeds with reference to the accompanying drawings.

BRIEF DESCRIPTION OF THE DRAWINGS

The embodiments of the invention are illustrated by way of example and not by way of limitation in the figures of the accompanying drawings in which like references indicate similar elements. It should be noted that references to "an" embodiment of the invention in this disclosure are not necessarily to the same embodiment, and they mean at least one.

FIGS. 7-24 are example familial risk matrices for determining familial risk of breast cancer.

DETAILED DESCRIPTION

Overview of Technologies

Figure 1:
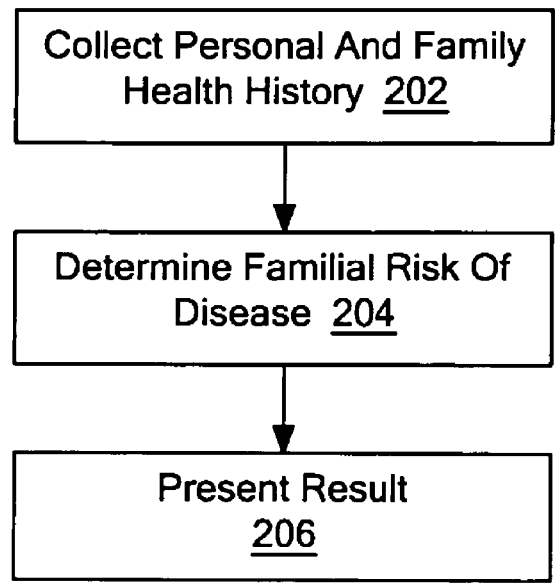
FIG. 1 is a flowchart showing an example method for determining familial risk of disease for a subject.

The technologies described herein can be used in a variety of scenarios in which determination of the familial risk of one or more diseases of interest is useful.

A disease of interest includes any disease for which familial risk is assessed for a subject. In practice, diseases of interest include common diseases that result from complex interactions of multiple genes with multiple environmental factors. For example, coronary heart disease, stroke, diabetes, colorectal cancer, breast cancer, and ovarian cancer can be diseases of interest.

An indicator disease includes any disease associated with indicating or otherwise correlating with the risk of developing a disease of interest. For example, ovarian cancer can be an indicator disease for breast cancer, and coronary heart disease can be an indicator disease for stroke.

An indicator trait includes any trait associated with indicating or otherwise correlating with the risk of developing a disease of interest. For example, smoking can be an indicator trait for lung cancer, smoking can be an indicator trait for heart disease, a mutation in the MSH2 gene or MLH1 gene can be an indicator trait for colorectal and endometrial cancer, and Ashkenazi Jewish ancestry can be an indicator trait for breast and ovarian cancer.

A first-degree relative includes blood relatives, such as parents, siblings, or children. First-degree relatives share one half of their genes in common.

A second-degree relative includes aunts, uncles, nieces, nephews, half-siblings, and grandparents. Second-degree relatives share one quarter of their genes in common.

Family health history information includes disease history of a subject's biological relatives. For example, family health history information can include disease history of first- and second-degree relatives, as well as disease history of more distant relatives. Disease history, for example, can include the number of first- and second-degree relatives, if a relative has or has had a disease of interest, indicator disease or indicator trait, sex of affected relatives, lineage of affected relatives (e.g., nuclear, maternal or paternal side of the family), type of affected relative (e.g., sibling or parent), and the age of the relative at time of diagnosis of a disease of interest, indicator disease or indicator trait.

Personal health history information includes demographic information such as age, date of birth, sex, and race/ethnicity; anthropometric and physiologic traits such as height, weight, waist circumference, blood cholesterol and blood pressure; medical history such as whether the subject currently has or previously has had a disease or a disease risk factor (e.g., a disease of interest or an indicator disease or trait); personal health behavior information, and the like; or any combination thereof.

Personal health behavior information includes information related to smoking, exercise, diet, screening tests, and the like.

Screening tests include any test that screens for disease or risk factors associated with disease. For example, screening tests can include clinical breast exams, mammograms, fecal occult blood tests, sigmoidoscopy, colonoscopy, blood cholesterol test, blood pressure test, blood sugar test, and the like.

Familial risk of disease includes a likelihood of developing a disease based on personal and family health histories. In other words, the familial risk of disease describes the strength of the personal and family health histories as a risk factor for a disease of interest. For example, familial risk of a disease of interest can be categorized as high (e.g., strong), moderate, or low (e.g., weak) based on the number of first- and second-degree relatives having the disease of interest, an indicator disease or indicator trait, and the relatives' age of onset of the disease of interest or indicator disease, and the like. For most common diseases, compared to weak familial risk, having a moderate familial risk may be associated with about a 2-fold increase, and having a strong familial risk may be associated with about a 3-fold or greater increase in risk.

A predetermined personal disease history scenario includes any personal health history information that may be associated with increased or decreased risk for a disease of interest. For example, having a personal history of a disease of interest at an early age of onset and having an indicator trait can be a predetermined personal disease history scenario, and having a personal history of an indicator disease associated with a disease of interest at a late age of onset can be a predetermined personal disease history scenario.

A predetermined familial disease history scenario includes any family health history information that may be associated with increased or decreased risk for a disease of interest. For example, having a first-degree relative with a disease of interest at a late age of onset can be a predetermined familial disease history scenario, and having two second-degree relatives from the same lineage with an indicator disease at an early age of onset is another example of a predetermined familial disease history scenario.

Intersection of predetermined personal and familial disease history scenarios includes situations in which the predetermined personal and familial disease history scenarios are referenced with one ore more familial risk matrices for the disease of interest. According to an embodiment of the invention, for any given predetermined personal disease history scenario, a minimum of two predetermined familial disease history scenarios that describe family history information will meet in a familial risk-indicating cell within the matrix. The level of familial risk (e.g., weak, moderate or strong) is assigned based on the intersection of the three scenarios As an example, a three dimensional matrix may be defined whose "axes" are 1) personal disease history scenarios, 2) first familial disease history scenarios, and 3) second familial disease history scenarios. Note that for any given predetermined personal disease history scenario the assigned familial risk of disease of interest could be based on several intersections obtained from several different predetermined familial disease history scenarios identified within a matrix for a disease of interest. In that case, the cell with the highest magnitude of risk is selected in order to assign the familial risk of disease.

Familial risk clarifiers include qualifying statements, which clarify or further explain the assignment of familial risk of a disease of interest by describing the elements of the personal or family history that are associated with the level of familial risk, and the possibility that the personal and family histories are suggestive of an inherited syndrome. For example, familial risk clarifiers can be used in the explanation of familial risk to subjects and health professionals, can inform genetic testing decisions, and can be used to tailor a disease prevention plan.

EXAMPLES

In any of the examples herein, an age of onset of disease or age at first diagnosis of a disease or trait can be an age range, particular age, age category (e.g., early, late, or the like), or other indication of age. Although particular ages are shown in some examples (e.g., early-onset, late-onset), other ages can be used.

Example 1

Example Method for Determining Familial Risk of Disease of Interest for a Subject FIG. 1 shows an example method 200 for determining familial risk of disease for a subject.

At 202, personal and family health histories are collected. For example, disease history of a subject and a subject's first- and second-degree biological relatives can be collected, including the sex of the subject, and the number, sex, type and lineage of the subject's first- and second-degree relatives, and whether the subject or a relative has or has had the disease of interest, or an indicator disease or indicator trait associated with that disease of interest, and the age of the subject and relative at the time of first diagnosis or onset of the disease of interest, indicator disease or indicator trait.

At 204, familial risk of the disease of interest is determined by analyzing personal and family health histories. For example, predetermined personal and familial disease history scenarios can be analyzed.

At 206, results of the determination of the familial risk of a single disease of interest are presented. For example, the familial risk of a disease of interest can be presented as high (e.g., strong), moderate, or low (e.g., weak). Familial risk clarifiers can also be presented.

The method described in this or any of the other examples can be a computer-implemented method performed via computer-executable instructions in one or more computer-readable media. Any of the actions shown can be performed by software incorporated within an electronic medical record system or any other health information system, or a database supporting clinical trials or epidemiologic research.

Example 2

Figure 2:
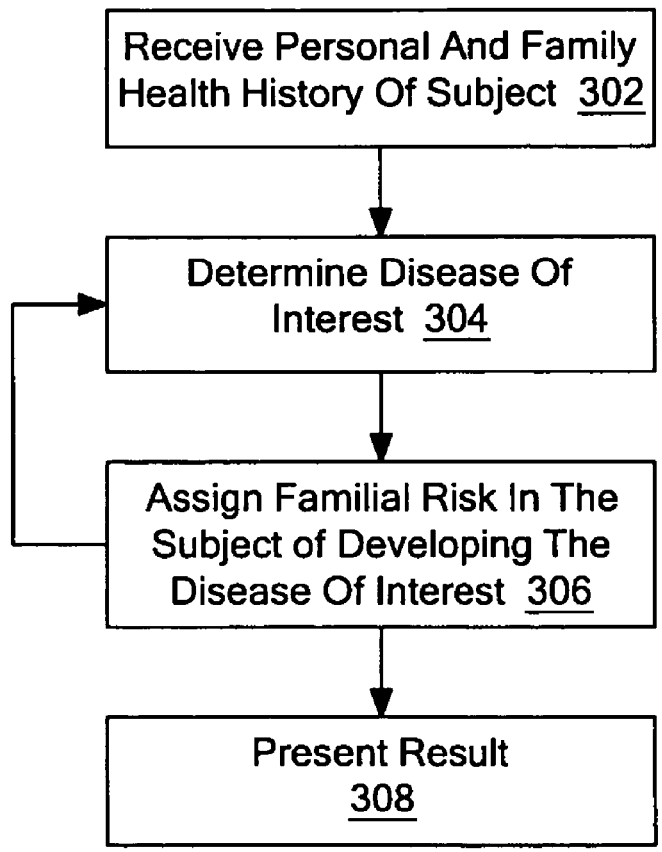
FIG. 2 is a flowchart showing an example method for determining familial risk of one or more diseases of interest for a subject.

Example Method for Determining Familial Risk of One or More Diseases of Interest for a Subject FIG. 2 shows an example method 300 for determining the familial risk of one or more diseases of interest for a subject.

At 302, personal and family health histories of a subject are received. For example, disease history of a subject and a subject's first- and second-degree biological relatives can be received, including the number, lineage, type and sex of first- and second-degree relatives, and whether the subject or a relative has or has had diseases of interest, or an indicator disease or an indicator trait associated with those diseases of interest, and the age of the subject and relatives at the time of first diagnosis or onset of the diseases of interest, indicator diseases or indicator traits.

At 304, a disease of interest is determined. For example, heart disease, stroke, diabetes, colorectal cancer, breast cancer, and ovarian cancer can be diseases of interest that are determined.

At 306, the familial risk of the determined disease of interest can be assigned for a subject. For example, the personal health history of a subject and the family health history of a subject's first- and second-degree biological relatives can be analyzed to assign the level of familial risk for the disease of interest. Following the assignment of the familial risk for the determined disease of interest, one or more additional diseases of interest can be determined at 304, and the level of familial risk for the one or more additional diseases of interest can be assigned.

At 308, results of the assignment of the familial risk for the one or more diseases of interest can be presented. For example, the familial risk can be categorized as low (e.g., weak), moderate, or high (e.g., strong) and presented to the subject with accompanying familial risk clarifiers.

Example 3

Figure 3:
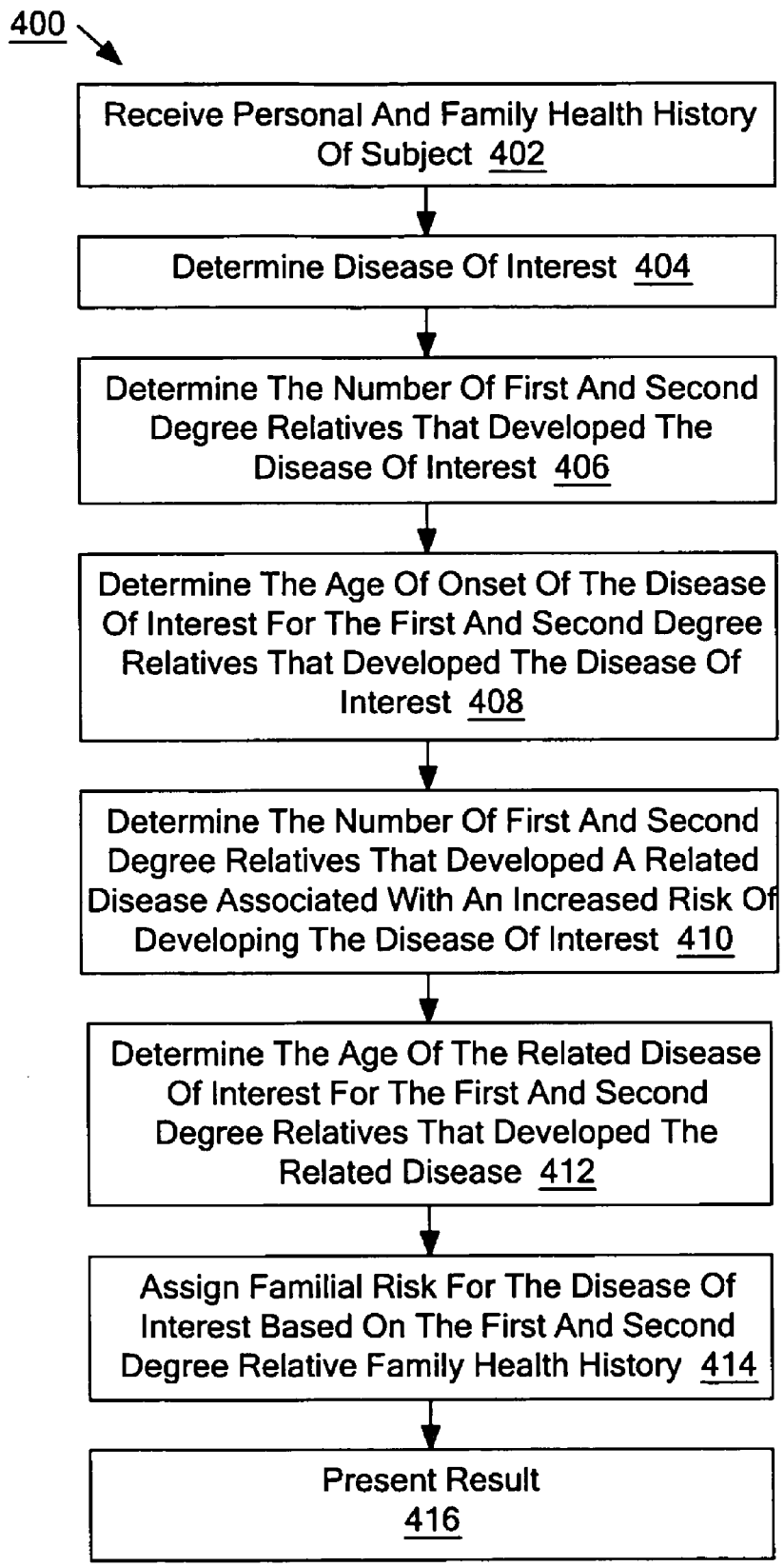
FIG. 3 is a flowchart showing an example method for determining a subject's familial risk of a disease of interest based on first- and second-degree relative family health history.

Example Method for Determining a Subject's Familial Risk of a Disease of Interest Based on Personal Health History and First- and Second-Degree Relative Family Health History FIG. 3 shows an example method 400 for determining a subject's familial risk of a disease of interest based on personal health history and first- and second-degree relative family health history.

At 402, personal and family health histories for a subject are obtained. Personal and family health histories can be obtained in real-time from the subject or another historian (e.g., a family member) or via the subject's paper or electronic health records, or from paper or electronic forms used for clinical or epidemiological research. For example, personal and family health histories for a subject can be obtained via completed questionnaires in an electronic or paper format.

At 404, a disease of interest is determined, for example by the consumer herself or by a health professional or researcher. For example, heart disease, stroke, diabetes, colorectal cancer, breast cancer, and ovarian cancer can be diseases of interest that are determined.

At 406, whether a subject has or has had the disease of interest is determined from the personal health history, and the number of first- and second-degree relatives that have or have had the disease of interest is determined from the family health history.

At 408, if the subject has or has had the disease of interest, then the age of onset of the disease of interest is determined from the personal health history, and if first- and second-degree relatives have or have had the disease of interest, then the age of onset of the disease of interest is determined from the family health history. Lineage and sex of the first- and second-degree relatives that developed the disease of interest are also determined.

At 410, whether a subject has or has had a different disease associated with the disease of interest (e.g., an indicator disease) is determined from the personal health history, and the number of first- and second-degree relatives that have or have had an indicator disease is determined from the family health history.

At 412, if the subject has or has had an indicator disease, then the age of onset of the indicator disease is determined from the personal health history, and if first- and second-degree relatives have or have had the indicator disease, then the age of onset of the indicator disease is determined from the family health history. Lineage and sex of the first- and second-degree relatives that have or have had the indicator disease are also determined.

At 414, a subject's familial risk of the disease of interest based on the personal health history and first- and second-degree relative family health history is assigned. For example, the familial risk can be assigned as low (e.g., weak), moderate, or high (e.g., strong) based on the personal and family health histories (e.g., by detection of the intersection of predetermined personal and familial disease history scenarios).

At 416, results of the assignment of familial risk for one or more diseases of interest can be presented. For example, familial risk can be categorized as low (e.g., weak), moderate, or high (e.g., strong) and presented to the subject with accompanying familial risk clarifiers.

Example 4

Figure 4:
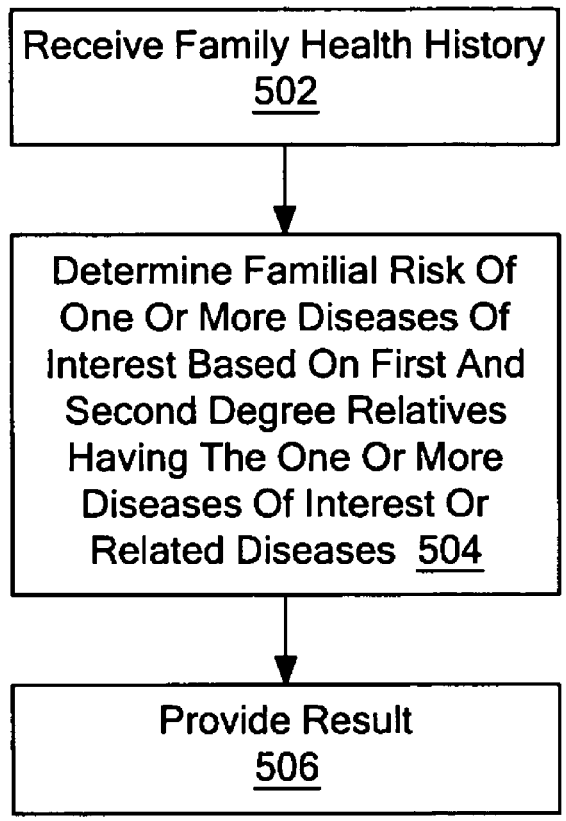
FIG. 4 is a flowchart showing an example computer-implemented method for determining familial risk of one or more diseases of interest.

Example Computer-Implemented Method for Determining Familial Risk of One or More Diseases of Interest FIG. 4 shows an example computer-implemented method 500 for determining the familial risk of one or more diseases of interest.

At 502, personal health history and family health history is received. For example, disease history of a subject and a subject's first- and second-degree biological relatives can be received, including the number, sex, type, and lineage of first- and second-degree relatives, and whether the subject or a relative has or has had a disease of interest or an indicator disease or indicator trait associated with the disease of interest, and the age of the relative at the time of first diagnosis or onset of the disease of interest or indicator disease or trait.

At 504, the familial risk of one or more diseases of interest is determined based on personal health history and first- and second-degree family health history of one or more diseases of interest or indicator diseases or indicator traits.

At 506, results of the assignment of the familial risk for the one or more diseases of interest can be presented. For example, the familial risk can be categorized as low (e.g., weak), moderate, or high (e.g., strong) and presented with accompanying familial risk clarifiers.

Example 5

Figure 5:
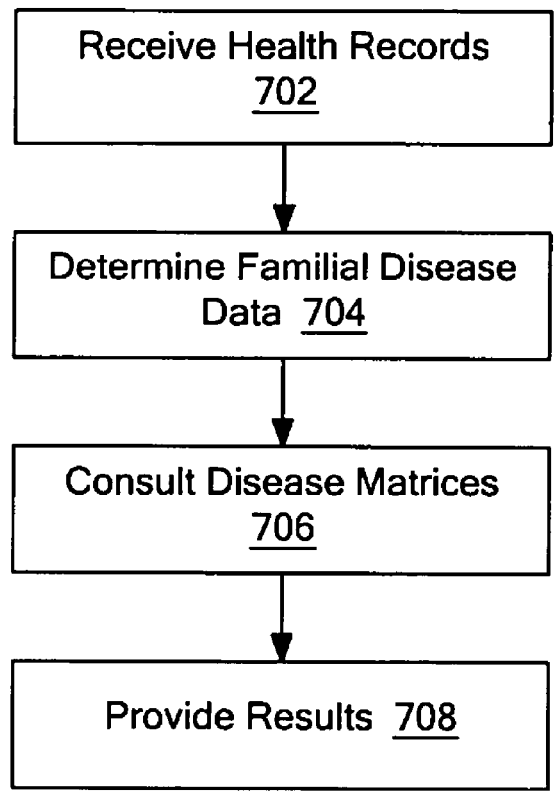
FIG. 5 is a flowchart showing yet another example method for determining familial risk of disease for a subject.

Another Example Method for Determining Familial Risk of a Disease of Interest for a Subject FIG. 5 shows another method 700 for determining the familial risk of a disease of interest for a subject.

At 702, health records are received. For example, personal health history records and health records of one or more relatives can be received. The health records can include the disease history of a subject and a subject's first- and second-degree biological relatives, including the number, sex, type, and lineage of first- and second-degree relatives, and whether the subject or a relative has or has had a disease of interest, or an indicator disease or indicator trait associated with that disease of interest, and the age of the subject or relative at the time of first diagnosis or onset of the disease of interest, indicator disease or indicator trait. Additionally, health records can include personal health history information such as age, date of birth, sex, race/ethnicity, height, weight, and personal health behavior information, or any combination thereof.

At 704, familial disease data can be determined from the health records received. For example, disease history of a subject and a subject's first- and second-degree biological relatives can be determined, including the number, sex, type, and lineage of first- and second-degree relatives, and whether the subject or a relative has a disease of interest or an indicator disease or indicator trait associated with that disease of interest, and the age of the subject or relative at the time of first diagnosis or onset of the disease of interest, indicator disease or indicator trait.

At 706, familial risk matrices for one or more diseases of interest can be consulted to determine the familial risk of one or more diseases for the subject based on the determined familial disease data. For example, predetermined personal and familial disease history scenarios (e.g., disease data on the subject and first- and second-degree relatives) can be compared to the familial risk matrices (e.g., matrices that assign a level of familial risk for a disease of interest) by identifying the intersections of predetermined personal and familial disease history scenarios.

At 708, results of the consultation of the familial risk matrices for one or more diseases of interest can be provided as results of the determination of the familial risk of disease. For example, an intersection of one predetermined personal disease history scenario and two predetermined familial disease history scenarios can result in an assignment of a level of familial risk. Additionally, familial risk clarifiers can be provided with the results to clarify or further explain the determination of the familial risk of disease.

Example 6

Figure 6:
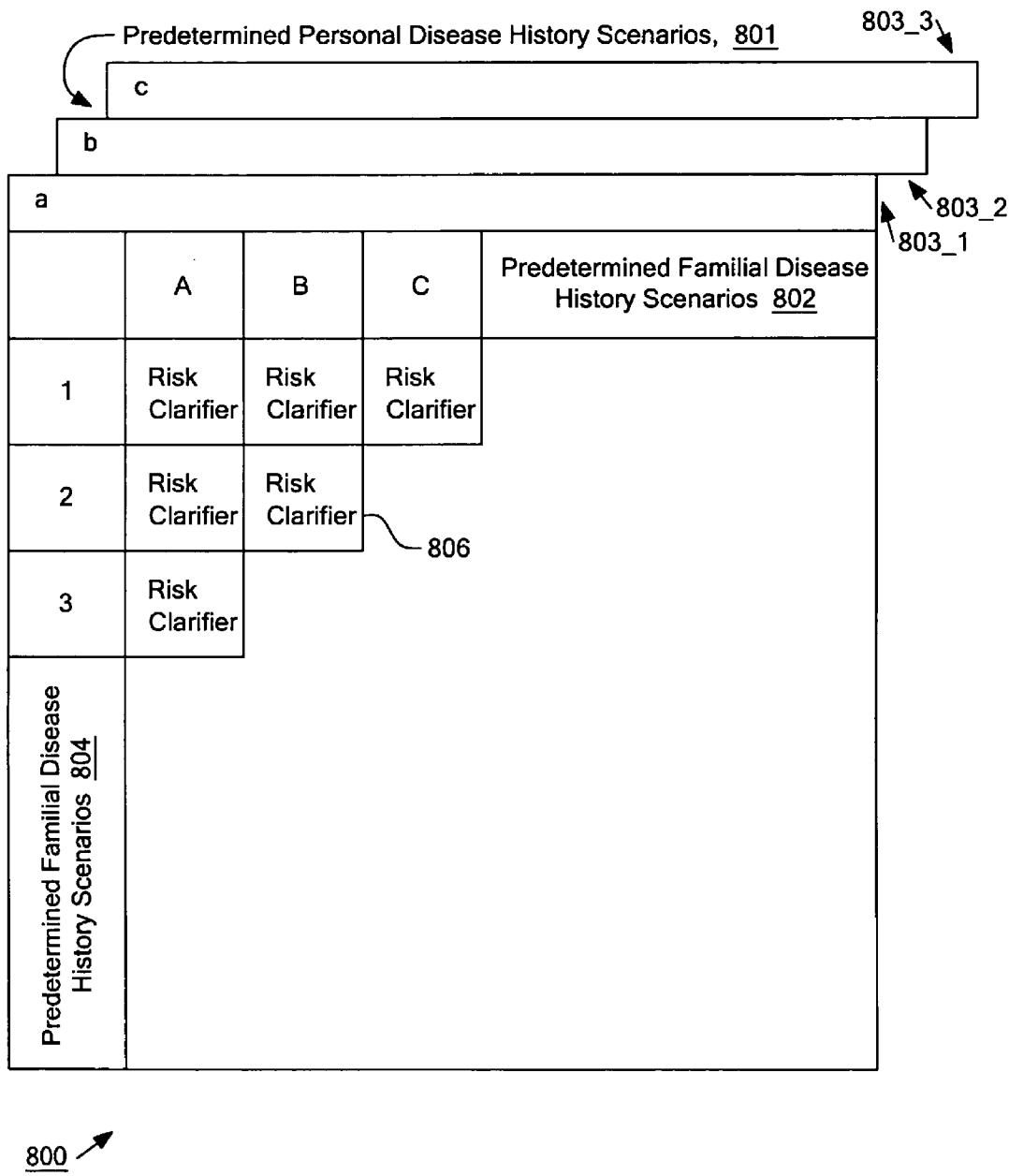
FIG. 6 illustrates an example familial risk matrix for determining familial risk of disease based on personal and family health histories.

Example Familial Risk Matrix for Determining the Familial Risk of a Disease of Interest Based on Personal and Family Health History FIG. 6 illustrates an example familial risk matrix 800 for determining the familial risk of a disease of interest based on personal health history and family health history. The matrix may also be referred to as an array. Such a matrix can be used as a look-up table to assess a subject's familial risk of a disease of interest in any of the examples herein.

In this example, the familial risk matrix 800 is a conceptual, three-dimensional ("3D") matrix or array: One "axis" of the 3D matrix includes predetermined personal disease history scenarios 801 (e.g., a, b, c, . . . ), another axis of the matrix includes predetermined familial disease history scenarios 802 (e.g., A, B, C, . . . ) and the third axis of the matrix includes predetermined familial disease history scenarios 804 (e.g., 1, 2, 3 . . . ). The matrices 803_1, 803_2, . . . represented by the combination of different scenarios may be of different sizes and may have different qualities, that is they need not all refer to the same set of personal and/or familial disease history scenarios.

The predetermined familial disease history scenarios 804 and 802 can be based on the number of first- and/or second-degree relatives from one lineage (e.g., nuclear, maternal or paternal) having a disease of interest, an indicator disease or indicator trait, the age of the relative at the time of first diagnosis or onset of the disease of interest, the indicator disease or indicator trait, and the type and sex of the relative. In matrices in which breast cancer or ovarian cancer is the disease of interest, for example, Ashkenazi Jewish ancestry is an indicator trait that can also be included in a predetermined personal or familial disease history scenario, i.e. in any one or more of scenarios 801, 802, and 804.

The intersection of two predetermined familial disease history scenarios 802, 804 in the context of a predetermined personal disease history scenario 801, such as (a, B, 2), results in a cell 806, which includes a risk assessment category (e.g., "Risk") being assigned based on the intersection of the three scenarios. In the preferred embodiment of the invention, one of only three levels of familial risk for a disease of interest can be assigned (represented by uppercase letters): low or weak familial risk (A), moderate familial risk (M), or strong or high familial risk (H). If more than one intersection is found within a matrix, then the intersection with the highest level of risk will determine the assigned level of familial risk. Furthermore, familial risk clarifiers (e.g., "Clarifiers") can be included with the assignment of risk, thereby incorporating references to qualifying statements which clarify or further explain the assignment of familial risk of disease based on the intersection of at least one predetermined personal disease history scenario and two predetermined familial disease history scenarios. Such familial risk clarifiers can be represented by lower case letters in the matrix and the references incorporated into the providing and presentation of results. Such familial risk clarifiers can be provided according to a hierarchy that considers the relevant family history characteristics or patterns of disease in the family without redundancy or inconsistencies, as described in detail below.

Analysis of multiple intersections of two predetermined familial disease history scenarios in the context of a personal disease history scenario can result in an overall familial risk level determination for the disease of interest. In the preferred embodiment of the invention, the highest familial risk level determined can be selected as the overall familial risk level determination for the disease of interest.

The creation of familial risk matrices for a disease of interest, such as breast cancer, are described in detail below. The method of familial risk stratification using the matrices described herein can be utilized for any disease of interest if personal and/or family health histories are risk factors for the disease of interest.

In constructing such matrices, the basic structure may remain constant, representing the elements of a family tree (pedigree), for example including the index case, first-degree relatives and second-degree relatives. (More distant relatives can be included if such information adds value to the risk assessment, although for most diseases this is not the case). What may vary in the structure of the matrices, for any given disease of interest, are the types and numbers of indicator diseases or indicator traits represented, as well as the relevance of age of onset of a disease of interest or indicator disease or indicator trait (e.g., may not be relevant at all, specific ages might be relevant, or several age groupings may be represented), and the sex of relatives or the type of relative (e.g., mother versus father) with a disease of interest or indicator disease or indicator trait may be represented.

Rules regarding identification of the lineage of relatives may be consistently followed for matrices of any given disease of interest, as this allows for recognition of patterns of disease transmission (including diseases of interest and indicator diseases), such as autosomal dominant, autosomal recessive and X-linked modes of transmission, that are suggestive of known hereditary syndromes that can feature the disease of interest.

For any given disease of interest, the presence or absence of that disease of interest, and indicator diseases and indicator traits associated with that disease of interest, in a subject or a subject's relatives, are represented by the intersections of personal and familial disease history scenarios within a matrix. For any given disease of interest, a standard set of rules is followed to determine the strength of the assigned familial risk level (e.g., weak, moderate, or strong) represented by each of the possible intersections or cells within a matrix. The basis for these rules of familial risk assignment is derived from empirical data describing personal and family history characteristics that are specific to the disease of interest, or when such data are not available, general principles of familial risk assessment are followed. As new knowledge regarding personal and family history characteristics associated with a disease of interest becomes available, the level of familial risk assigned and/or the clarifying statements explaining the familial risk assignment might change.

The structure of the familial risk matrices and the rules used to determine familial risk stratification for a disease of interest allow for flexibility to make changes in the matrices with relative ease to accommodate new knowledge regarding those aspects of the familial risk stratification method which can vary, such as inclusion of more distant relatives, change in the numbers and types of indicator diseases or indicator traits, change in the age of onset criteria, representation of the sex of relatives or the types of relatives within the matrices, or change in the level of familial risk and the clarifying statements represented within any given cell within the matrix that represents an intersection of two predetermined familial risk scenarios within the context of a predetermined personal disease history scenario.

Example 7

Example Familial Risk Matrices for Determining Familial Risk of Breast Cancer Based on Personal and Family Health Histories FIGS. 7-24 illustrate example familial risk matrices (according to the form of example familial risk matrix (800) for determining familial risk of breast cancer based on personal health history and family health history. Shaded areas of the matrices are duplicative cells that contain redundant information found within each matrix. Note that by recognition of disease associations and patterns in personal health history and family history that relate to other diseases, an approach similar to the above can be taken to generate familial risk matrices for other diseases, e.g., coronary heart disease, stroke, colorectal cancer etc.

In the example, the definition of age of onset of breast cancer is defined as:

Breast cancer: early, <age 50; late, > or =age 50 or age of onset unknown

In the example, the definition of lineage is:

Nuclear: any combination of index case, siblings, or children

Maternal: any combination of mother, mother's siblings, or at least one of mother's parents. Can include index case, index case's siblings and index case's children Paternal: any combination of father, father's siblings, or at least one of father's parents. Can include index case, index case's siblings and index case's children.

The familial risk stratification matrices for breast cancer recognize family history characteristics that are associated with an increased risk of breast cancer, as well as patterns of disease suggestive of hereditary syndromes that feature breast cancer. The family history characteristics associated with increased risk of breast cancer are derived from the literature. There are at least six hereditary syndromes that feature breast cancer. The two most common forms of hereditary syndromes that feature breast cancer are hereditary breast-ovarian cancer (HBOC) and hereditary site-specific breast cancer. Both are associated with germline BRCA1 and BRCA2 mutations. Most families with HBOC have BRCA mutations, and about half of families with hereditary site-specific breast cancer have BRCA mutations. The breast cancer familial risk matrices in FIGS. 7-24 recognize familial characteristics that are associated with an increased risk of breast cancer, as well as the two common familial syndromes that feature breast cancer. With the addition of other indicator diseases in the matrices, additional family history associated with breast cancer could be identified, and other rare hereditary syndromes that feature breast cancer could be recognized. For example, familial aggregation of breast, endometrial and thyroid cancer is suggestive of Cowden syndrome due to mutations in the PTEN gene. Familial aggregation of breast, brain, adrenalcortical cancer and sarcoma is suggestive of Li-Fraumeni syndrome due to mutations in the TP53 gene.

The breast cancer familial risk matrix in FIGS. 7-24 is arranged as six (6) sets of three, two-dimensional tables or matrices. These correspond to eighteen (18) tables depicted in FIGS. 7-24, respectively.

The first set of tables consists of FIGS. 7-9. These are applicable to a female user who has or has had both early onset breast cancer and ovarian cancer (as the personal disease history scenario). The Y-axis (familial disease history scenarios) is the same for FIGS. 7 and 8, focusing on $1^{st}$ degree relatives of the user, whereas the Y-axis of FIG. 9 focuses on her $2^{nd}$ degree relatives. The X-axis in FIG. 7 focuses on $1^{st}$ degree relatives, whereas the X-axis in both FIGS. 8 and 9 deals only with $2^{nd}$ degree relatives. Note that the assessed familial risk in all possible intersections of the first set is H (high), but there are differences in the risk clarifiers contained in the intersections. An element of a matrix may include, in addition to the risk level assignment, a reference to one or more risk clarifiers that explain the risk level assigned by that element.

Familial risk clarifiers for the breast cancer matrices in FIGS. 7-24 include:

a=At least one family member with both breast and ovarian cancer. The combination of these cancers is a risk factor for breast cancer and can be a sign of an inherited form of breast cancer called hereditary breast-ovarian cancer.

b=Closely related family members with breast and ovarian cancer. The combination of these two cancers is a risk factor for breast cancer and can be a sign of an inherited form of breast cancer called hereditary breast-ovarian cancer.

c=Two or more closely related family members with ovarian cancer. Although a different cancer, a family history of ovarian cancer is a risk factor for breast cancer and can be a sign of an inherited form of breast cancer called hereditary breast-ovarian cancer.

d=At least one family member with male breast cancer, which can be a sign of an inherited form of breast cancer.

e=At least one family member with breast cancer at a young age.

f=Two or more closely related family members with breast cancer.

g=A family member with breast cancer at a later age.

h=A family member with ovarian cancer, which can be a risk factor for breast cancer.

i=Three or more closely related family members with breast cancer.

j=Some inherited forms of breast and ovarian cancer are more common in Ashkenazi Jewish families.

k=Your personal history suggests the possibility of an inherited form of cancer, which might increase your risk for developing another cancer.

In all of the tables of FIGS. 7-24, if the assigned familial risk at an intersection is H and the user is Ashkenazi Jewish, then each element may also contain the j clarifier.

Turning now to FIGS. 10-12, these three tables are used to look up an assigned familial risk level when a female user has or has had both late-onset breast cancer and ovarian cancer. For such a user, the tables in FIGS. 7-9 are not applicable. The X and Y axis scenarios of FIGS. 10-12 are however the same as in FIGS. 7-9, respectively. Once again, the assessed familial risk in all intersections is H, but there are differences in the risk clarifiers, depending on the user's personal and family disease history.

Turning now to FIGS. 13-15, these three tables are used to look up an assigned familial risk level when a female user has or has had early-onset breast cancer and has no history of ovarian cancer, or when a male user has or has had breast cancer at any age of onset. The X and Y axis scenarios are the same as in FIGS. 7-9, respectively. For such a user, the tables in FIGS. 7-12 are not applicable. Once again, the assessed familial risk in all intersections is H, but there are differences in the risk clarifiers, depending on the user's personal and family disease history.

The three tables in FIGS. 16-18 are used to look up an assigned familial risk level when a female user has or has had late-onset breast cancer and no history of ovarian cancer. The X and Y axis scenarios are the same as in FIGS. 7-9, respectively. For such a user, the tables in FIGS. 7-15 are not applicable. The assessed familial risk is generally H except for a small number of cases where there are no first- or second-degree relatives with breast and ovarian cancer (see for example element 4-045 in FIG. 16). Note the differences in the risk clarifiers between elements 4-153 and 4-154 in FIG. 18, depending on the user's personal and family disease history.

The tables in FIGS. 19-21 are used when a female user has or has had ovarian cancer and no history of breast cancer.

The tables in FIGS. 22-24 are used when a user has no personal history of breast or ovarian cancer.

Example 8

Example Hierarchy of Presentation of Familial Risk Clarifiers in Familial Risk Matrices for Determining Familial Risk of Breast Cancer Based on Personal and Family Health History Familial risk clarifiers in familial risk matrices for determining familial risk of breast cancer (for instance, according to Example 7 based on personal health history and family health history) can be provided according to a hierarchy to ensure appropriate presentation of explanations of the level of familial risk without redundancy or inconsistencies. For example, a hierarchy utilizing familial risk clarifiers described in Example 7 can be as follows:

Familial risk clarifier "a" can be presented;
Familial risk clarifier "b" can be presented;
Familial risk clarifier "c" can be presented;
Familial risk clarifier "d" can be presented;
Familial risk clarifier "e" can be presented;
Familial risk clarifier "f" can be presented when familial risk clarifier "i" is not presented;
Familial risk clarifier "g" can be presented if:
  Familial risk clarifier "a" is not presented; or Familial risk clarifier "b" is not presented; or Familial risk clarifier "d" is not presented; or Familial risk clarifier "e" is not presented; or Familial risk clarifier "f" is not presented; or Familial risk clarifier "i" is not presented;
Familial risk clarifier "h" can be presented if:
  Familial risk clarifier "a" is not presented; or Familial risk clarifier "b" is not presented; or Familial risk clarifier "c" is not presented;
Familial risk clarifier "i" can be presented;
Familial risk clarifier "j" can be presented; and
Familial risk clarifier "k" can be presented.

Example 9

Example Advantages and Applications of Technologies

While family history is a risk factor for most chronic diseases of public health significance, it is underutilized in clinical and epidemiological investigations of diseases, and in the practice of preventative medicine and public health for assessing disease risk and influencing early detection and prevention strategies. Geneticists have long recognized the value of family history for discovering inherited disorders, which are usually the result of single gene mutations. Although single gene disorders are typically associated with a large magnitude of risk, they account for only a small proportion of individuals with a genetic risk for common, chronic diseases. Most of the genetic susceptibility to these disorders for most people is the result of multiple genes interacting with multiple environmental factors (broadly defined as diet, exposures, behaviors, etc.). Family history therefore, is more than genetics; it reflects the consequences of inherited genetic susceptibilities and shared environment. All of these factors are important when estimating disease risk.

It is well known that people with close relatives with certain diseases such as heart disease, diabetes, and cancers, are more likely to develop those diseases themselves. Studies suggest that having a first-degree relative with a chronic disease can at least double a person's risk of developing the same or a related disease compared to someone without this history. This risk generally increases with an increasing number of affected relatives, especially if their disease was diagnosed at an early age. Physicians usually collect information about a patient's family history, but often do not discuss, revisit or update it over time. As a result, they may miss opportunities to offer specific management and prevention recommendations for diseases that run in the family. An embodiment of the invention uses personal and family health histories as a "genomics tool" that can capture the interactions of genetic susceptibilities and environmental risk factors shared by family members. Determining the familial risk for a disease (i.e., defining the strength of an individual's personal and family health history as a disease risk factor) can aid in making personalized recommendations for disease management and prevention, which should result in improved health outcomes.

Healthcare information and resources are widely available to medical providers and patients via electronic and printed resources. Unfortunately, many informational sources provide only broad, generalized information. An embodiment of the invention provides users with feedback regarding individualized risk assessment that is applicable to their own personalized health care, while also being simple and easy to use and interpret. Systems and methods for collecting information about an individual's personal and family health histories that determine the strength of this information as a risk factor for a disease, and clarify the aspects of the history that are associated with the disease or are suggestive of hereditary syndromes that can feature the disease, can influence the clinical management and prevention of disease, and can provide risk stratification in clinical trials and epidemiologic investigations. Prevention strategies can include targeting lifestyle changes such as diet, exercise, and smoking cessation; screening at earlier ages, more frequently, and with more intensive methods than might be used for average-risk individuals; use of chemoprevention such as aspirin for heart disease or Tamoxifen for breast cancer; and referral to a specialist for assessment of genetic risk factors, including genetic testing.

Currently there is no standardized way to collect or interpret family health history data for clinical practice or for use in clinical or epidemiologic research. Most healthcare professionals and researchers collect family history information using paper-based tools that ask questions such as, "Do you have any first-degree relative with breast cancer?" and the clinicians and researchers often limit their interpretation of the collected data to "family history positive" or "family history negative" for the disease of interest without stratifying the familial risk. In Addition, the Interpretation May not Consider the presence of indicator diseases or traits that could influence the risk of disease, or recognition of patterns of disease that may be suggestive of inherited syndromes.

Risk assessment tools that are used in clinical practice and research may also collect limited family history data resulting in limited interpretation of family history. For example, the Gail model projects a woman's individualized estimate of risk for invasive breast cancer over a 5-year period and over her lifetime (to age 90). The Gail model inquires about several risk factors such as current age, race/ethnicity, age at menarche, age at first live birth, whether there is a history of breast biopsy and if so how many and were there signs of atypia or hyperplasia on the biopsy, and family history. However, the family history is limited to asking how many first-degree relatives (i.e., mother or sisters) have had breast cancer. It does not ask about male breast cancer, or breast or ovarian cancer in children or second-degree relatives, which are important questions for determining the level of familial risk of breast cancer and the possibility of a hereditary syndrome that can feature breast cancer. In contrast, the Cancer-Gene genetic risk assessment tool for cancer collects family history data about first- and second-degree relatives such as their age, sex, and age at diagnosis of cancer, and this tool provides information regarding an absolute lifetime risk for cancer and it estimates the likelihood that an individual carries a mutation in one of the cancer predisposition genes. However, this tool does not interpret and present results regarding the strength of the personal and family history as a disease risk factor, which might be more easily understood and acted upon by consumers and health professionals, and it does not provide feedback describing the aspects of the personal and family health histories that are associated with the disease of interest including an explanation as to why a hereditary syndrome might be possible.

Familial risk assessment technologies that are in accordance with an embodiment of the invention can play a major role in clinical medicine and research by allowing clinicians and researchers the ability to measure the strength of the personal and family health histories as risk factors for a disease of interest for patients or research participants. Clinicians and researchers can use this information to stratify their populations according to the level of familial risk for a disease, which can inform analyses performed by the researcher or recommendations for disease management, early detection or prevention made by the clinician. Similarly, individuals have the ability to maintain and update their personal and family health history records at their convenience (e.g., at home) and they can discuss the implications of their familial risk assessment for one or more diseases with their healthcare providers during visits.

The technology can be used on a standalone computer system or via networked computers via local networks and/or the Internet increasing the opportunities for evidence-based medicine to be integrated into medical practice on a daily basis. The technology can be integrated within a researcher's database or a healthcare administration's electronic medical records or information systems allowing for increased data access and interchange. Such applications and technology also lend themselves to personalized medicine, home-based health management, including personal health records.

Example 10

Example Computer System for Conducting Analysis

Figure 25:
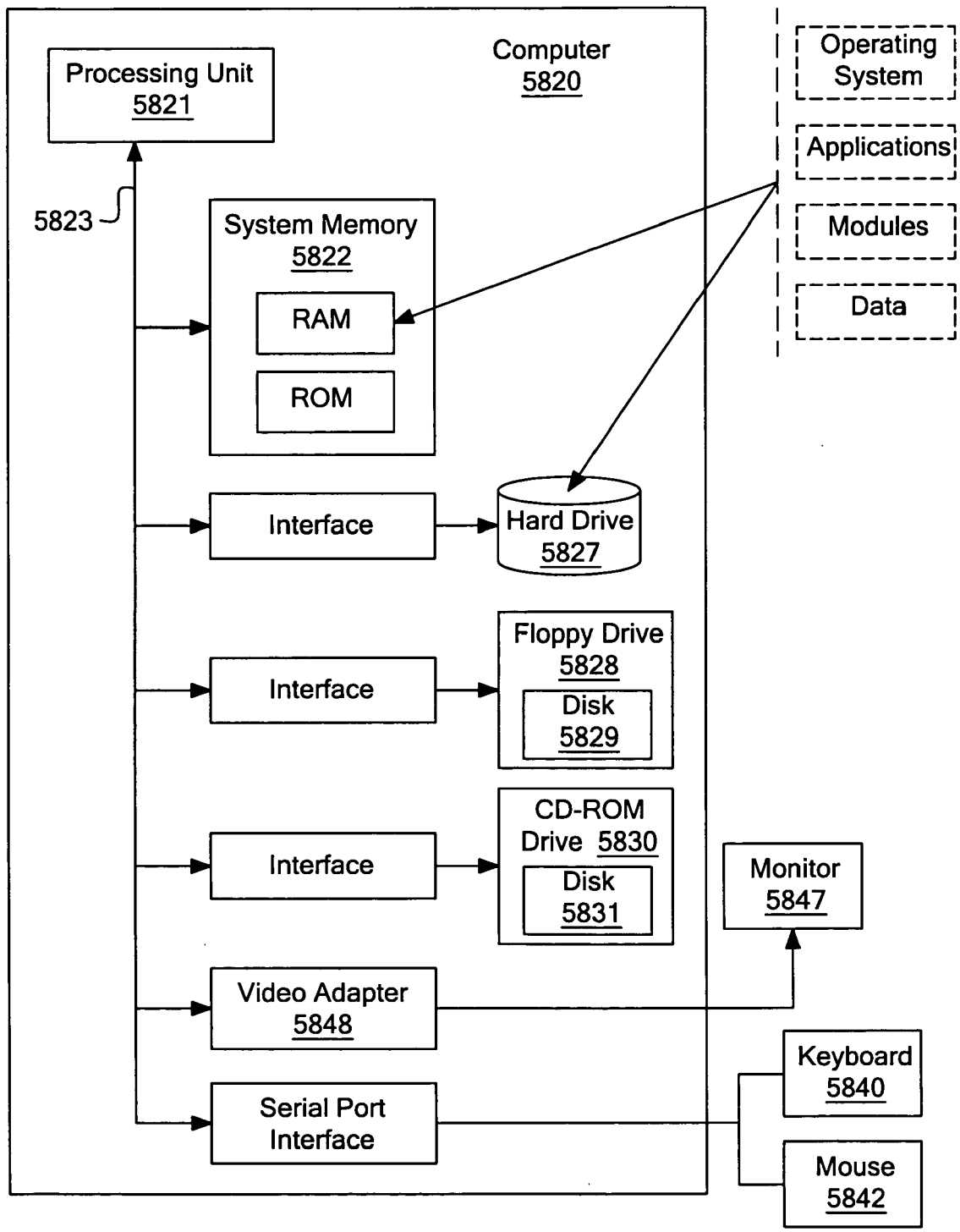
FIG. 25 is a block diagram of a computer system that can implement familial risk matrices and their uses.

FIG. 25 and the following discussion provide a brief, general description of a suitable computing environment for software (for example, computer programs) that can be written to implement the different embodiments of the invention described above. The methods described above can be implemented in computer-executable instructions (for example, organized in program modules). The program modules can include the routines, programs, objects, components, and data structures that perform the tasks and implement the data types for implementing the techniques described above.

While FIG. 25 shows a typical configuration of a desktop computer, the technologies may be implemented in other computer system configurations, including multiprocessor systems, microprocessor-based or programmable consumer electronics, minicomputers, mainframe computers, and the like. The technologies may also be used in distributed computing environments where tasks are performed in parallel by processing devices to enhance performance. For example, tasks can be performed simultaneously on multiple computers, multiple processors in a single computer, or both. In a distributed computing environment, program modules may be located in both local and remote memory storage devices. For example, code can be stored on a local machine/server for access through the Internet, whereby data from assays can be uploaded and processed by the local machine/server and the results provided for printing and/or downloading.

The computer system shown in FIG. 25 is suitable for implementing the technologies described herein and includes a computer 5820, with a processing unit 5821, a system memory 5822, and a system bus 5823 that interconnects various system components, including the system memory to the processing unit 5821. The personal computer 5820 can further include a hard disk drive 5827, a magnetic disk drive 5828, for example, to read from or write to a removable disk 5829, and an optical disk drive 5830, for example, for reading a CD-ROM disk 5831 or to read from or write to other optical media. The drives and their associated computer-readable media provide nonvolatile storage of data, data structures, computer-executable instructions (including program code such as dynamic link libraries and executable files), and the like for the personal computer 5820. Although the description of computer-readable media above refers to a hard disk, a removable magnetic disk, and a CD, it can also include other types of media that are readable by a computer, such as magnetic cassettes, flash memory cards, DVDs, and the like.

A user may enter commands and information into the personal computer 5820 through a keyboard 5840 and pointing device, such as a mouse 5842. Other input devices (not shown) may include a microphone, joystick, game pad, satellite dish, scanner, or the like. A monitor 5847 or other type of display device is also connected to the system bus 5823 via an interface, such as a display controller or video adapter 5848. In addition to the monitor, personal computers typically include other peripheral output devices (not shown), such as speakers and printers.

The above computer system is provided merely as an example. The technologies can be implemented in a wide variety of other configurations. Further, a wide variety of approaches for collecting and analyzing family history data and personal health data are possible. For example, the data can be collected and analyzed, and the results presented on different computer systems as appropriate. In addition, various software aspects can be implemented in hardware, and vice versa. Further, paper-based approaches to the technologies are possible, including, for example, purely paper-based approaches that utilize instructions for interpretation of algorithms, as well as partially paper-based approaches that utilize scanning technologies and data analysis software.

Example 11

Example Computer-Implemented Methods

Any of the computer-implemented methods described herein can be performed by software executed in an automated system (for example, a computer system). Fully-automatic (for example, without human intervention) or semi-automatic operation (for example, computer processing assisted by human intervention) can be supported. User intervention may be desired in some cases, such as to adjust parameters or consider results. Such software can be stored on one or more computer-readable media comprising computer-executable instructions for performing the described actions.

OTHER EMBODIMENTS AND ALTERNATIVES

The techniques described above classify and explain an individual's level of familial risk for one or more diseases of interest. An embodiment of the invention is a set of familial risk matrices (for a particular disease of interest) that are designed to ensure that everyone who is "looked up" in these matrices is classifiable regarding their familial risk; it is not limited to identification of only high-risk individuals or people that meet criteria for a specific hereditary syndrome.

One embodiment is a method for determining the extent to which personal and family health histories play a role in developing a disease of interest in a subject, the method comprising: obtaining the subject's personal and family health histories including one of the group consisting of history of the disease of interest, history of indicator diseases, and history of indicator traits; and referencing a familial disease risk matrix using the subject's obtained personal and family health histories to find the subject's assigned level of familial risk of the disease of interest.

Another embodiment is a comprehensive method of pedigree (personal and family history) analysis that assigns a level of familial risk for a disease of interest through recognition of patterns of disease in the personal and family medical histories of a subject that are associated with increased disease risk and/or inherited forms of a disease of interest. The method comprises: obtaining the history of a disease of interest or related condition(s), for a subject and his/her first- and second-degree relatives including the age (or age range) at which the disease or related condition(s) occurred, the sex of the subject or affected family member(s), and the lineage of the affected family member(s) (i.e., maternal, paternal, or nuclear); and referencing a hierarchical array of specific medical history characteristics, that pertain to a disease of interest, of (1) a subject and (2) all of his/her first-degree and (3) second-degree relatives, that considers all possible combinations of these medical history characteristics, where upon the intersections of the medical history characteristics of a subject and his/her first and second-degree relatives are each associated with a level of risk describing the family history (e.g., weak, moderate or strong), and through identification of all intersections that arise for any given subject for any given disease of interest, a determination can be made regarding the highest level of familial risk for a disease of interest. In such an embodiment, each intersection within the hierarchical array of the specific medical history characteristics, of a subject and his/her first- and second-degree relatives, may further give an explanation for the given level of familial risk, by citing the relevant family history characteristics, including the possibility that these characteristics may be suggestive of an inherited form of a disease.

In yet another embodiment of the invention, a comprehensive method of pedigree (personal and family history) analysis assigns a level of familial risk for a disease of interest through recognition of patterns of disease in the personal and family medical histories of a subject that are associated with increased disease risk and/or inherited forms of a disease of interest. The method comprises: obtaining the history of a disease of interest or related condition(s), for a subject and his/her first- and second-degree relatives including the age (or age range) at which the disease or related condition(s) occurred, the sex of the subject or affected family member(s), the type of affected family members, and the lineage of the affected family member(s) (i.e., maternal, paternal, or nuclear); and consulting tables that have displayed all possible combinations of specific medical history characteristics that pertain to a disease of interest, of (1) a subject, and (2) his/her first-degree relatives and (3) second-degree relatives, as hierarchical matrices where upon the intersections of specific medical history characteristics of a subject and his/her first- and second-degree relatives are each associated with a level of risk describing the strength of the personal and family histories (e.g., weak, moderate or strong) as a risk factor for the disease of interest. Through identification of all intersections that arise for any given subject for any given disease of interest, a determination can be made regarding the highest level of familial risk for a disease of interest. In such an embodiment, each intersection of medical history characteristics may further give an explanation for the given level of familial risk by citing the relevant personal and family history characteristics, including the possibility that these characteristics are suggestive of an inherited form of a disease.

In yet another embodiment, a machine-readable medium contains instructions stored therein which, when executed by a machine, implement an algorithm that determines the highest level of familial risk for a disease of interest for a subject. The algorithm automatically recognizes the intersections of specific medical history characteristics that pertain to a disease of interest of a subject and his/her first- and second-degree relatives that are associated with the highest level of familial risk, in response to items taken from the subject's personal and family history. Each intersection may further give an explanation for the given level of familial risk by citing the relevant personal and family history characteristics, including the possibility that these characteristics are suggestive of an inherited form of a disease, and when two or more intersections of medical history characteristics of the same level of familial risk are identified, all of the relevant explanations identified for each intersection of medical characteristics may be provided without redundancy or inconsistency according to an algorithm that considers all possible explanations of familial risk of a disease of interest.

It should be also be noted that the familial risk matrices, algorithms, or tables described above may be combined with other risk assessment techniques that consider other risk factors for disease, to give a more complete individualized risk assessment. Examples of such risk factor categories used by other risk assessment techniques include demographic factors (e.g., age, sex, ethnicity/race), physiologic and anthropometric measures (e.g., weight, height, waist circumference, blood pressure), laboratory test results (e.g., blood cholesterol, blood sugar), behaviors (e.g., smoking, exercise, diet), environmental exposures (e.g., second-hand smoke, ultraviolet radiation), and genetic markers (e.g., DNA-based genetic test results). As such, a personal and family history risk table or matrix may become part of a disease risk assessment tool that in effect has multiple dimensions. Such a tool uses demographic factors, behavior, environmental exposures and/or other scenarios in addition to personal and family health histories, to index into a multi-dimensional look-up table. The "intersection" in that case would be of at least four or more scenarios.

Having illustrated and described the principles of the invention in example embodiments, it should be apparent to those skilled in the art that the described examples are illustrative embodiments and can be modified in arrangement and detail without departing from such principles. Techniques from any of the examples can be incorporated into one or more of any of the other examples.

In view of the many possible embodiments to which the principles of the invention may be applied, it should be understood that the illustrative embodiments are intended to teach these principles and are not intended to be a limitation on the scope of the invention. For example, the functionality of a matrix, array, or look-up table may be implemented in a computer program using only if-then statements or using an expert system. I therefore claim as my invention all that comes within the scope and spirit of the following claims and their equivalents.

What is claimed is:

1. A computerized method for determining the extent to which personal and family health histories play a role in developing a disease of interest in a particular subject, the method comprising:

accessing, by a computer system, the particular subject's stored, personal and family health histories including a history of one of the group consisting of a) the disease of interest, b) indicator diseases, and c) indicator traits; and determining, by the computer system, the subject's assigned level of familial risk of the disease of interest by recognizing familial patterns of disease using a stored array of elements, wherein each element of the array gives a predetermined level of familial risk for the disease of interest corresponding to a different combination of a personal disease history scenario and a familial disease history scenario, wherein the predetermined level of risk was set based on having recognized familial patterns of disease, wherein said determining the subject's assigned level of familial risk of the disease of interest further comprises, indexing into the stored array of elements using a plurality of items taken from the subject's accessed personal and family health histories, to find one or more elements that match said plurality of items, wherein the items taken from the subject's accessed personal and family health histories include (a) whether any first- or second-degree relatives of the subject have developed the disease of interest, (b) whether any first- or second-degree relatives have developed an indicator disease, other than the disease of interest, associated with an increased risk of developing the disease of interest, and (c) for any first- or second-degree relative that developed the disease of interest or indicator disease, information comprising (i) an age of onset at which the disease of interest or indicator disease developed, (ii) a number of first-degree relatives of the subject that developed the disease of interest or indicator disease, and (iii) a number of second-degree relatives of the subject that developed the disease of interest or indicator disease.

2. The method of claim 1 further comprising:

compiling, by the computer system, clarifying statements that clarify or further explain the assigned level of familial risk of the disease of interest, wherein the compiled clarifying statements correspond to the same element of the array that was indexed and gave the assigned level of familial risk.

3. An article of manufacture comprising: a non-transitory machine-readable medium having instructions stored therein which program a computer system to access a particular subject's stored personal and family histories, recognize familial patterns of disease to determine an assigned level of familial risk of disease of interest for the particular subject based on having accessed the subject's stored personal and family histories, and present the assigned level of risk to a user, wherein the programmed computer system is to automatically provide the assigned level as including one of at least three different levels, wherein the stored instructions further program the computer system to perform a look-up in a multi-dimensional look-up table that comprises a plurality of personal disease history scenarios on a first axis of the table, a plurality of first degree familial disease history scenarios on a second axis of the table, a plurality of second degree familial disease history scenarios on a third axis of the table, and a plurality of table elements each of which represents a respective combination of the personal and first and second degree familial disease history scenarios and provides a predetermined level of familial risk for the disease of interest using the subject's accessed personal and family health histories, to read one of the table elements which represents the respective combination of the scenarios that matches the subject's accessed personal and family health histories, and then assign the predetermined level of familial risk encountered in the read table element to the subject, and wherein the plurality of first and second degree familial disease history scenarios comprise:

whether any first- or second-degree relatives have developed the disease of interest;

whether any first- or second-degree relatives have developed an indicator disease, other than the disease of interest, associated with an increased risk of developing the disease of interest; and for any first- or second-degree relative that developed the disease of interest or indicator disease, information comprising (i) an age of onset at which the disease of interest or indicator disease developed, (ii) a number of first-degree relatives of the subject that developed the disease of interest or indicator disease, and (iii) a number of second-degree relatives of the subject that developed the disease of interest or indicator disease.

4. The article of manufacture of claim 3 wherein the stored instructions implement a multi-dimensional familial risk matrix comprising:

a plurality of personal disease history scenarios on a first axis of the matrix;

a plurality of disease history scenarios for first degree family history on a second axis of the matrix;

a plurality of disease history scenarios for second degree family history on a third axis of the matrix; and a plurality of matrix elements each of which represents an intersection of the personal and first and second degree familial disease history scenarios and provides a predetermined level of familial risk for the disease of interest, wherein the programmed computer system accesses the matrix, using the subject's accessed personal and family health histories, to read a plurality of the matrix elements that intersect the scenarios for the subject's accessed personal and family health histories and then assigns the highest level of familial risk encountered in the read matrix elements, to the subject.

5. The article of manufacture of claim 4 further comprising stored instructions which program the computer system to automatically provide an explanation for the assigned level of familial risk, by citing relevant personal and family history characteristics of the subject, based on a reference stored in the read matrix elements.

6. The article of manufacture of claim 5 wherein the stored instructions program the computer system so that the explanation indicates the characteristics are suggestive of an inherited form of the disease of interest.

7. The article of manufacture of claim 4 further comprising stored instructions which program the computer system to automatically provide an explanation for the assigned level of familial risk, by citing relevant personal and family history characteristics of the subject.

8. The article of manufacture of claim 3, wherein the plurality of different levels include a low level, a medium level, and a high level.

9. A computer system comprising:

computer hardware that has been programmed to access a particular subject's stored personal and family histories and on that basis automatically recognize familial patterns of disease when assigning a level of familial risk of a disease of interest for the particular subject, and to present the assigned level of risk to a user, wherein the programmed computer hardware includes a look-up table whose input comprises a plurality of personal disease history scenarios and a plurality of familial disease history scenarios, the look-up table having a plurality table elements each of which is associated with a different combination of the personal and familial disease history scenarios and contains a predetermined level of familial risk for the disease of interest, said predetermined level having been set based on recognition of familial patterns of disease, wherein the programmed computer hardware is configured to perform a look-up using the subject's accessed personal and family health histories as input to the table, read one of the table elements that matches the subject's accessed personal and family health histories, and then assign the predetermined level of familial risk encountered in the read table element to the subject, and wherein the plurality of first and second degree familial disease history scenarios comprise:

whether any first- or second-degree relatives have developed the disease of interest;

whether any first- or second-degree relatives have developed an indicator disease, other than the disease of interest, associated with an increased risk of developing the disease of interest; and for any first- or second-degree relative that developed the disease of interest or indicator disease, information comprising (i) an age of onset at which the disease of interest or indicator disease developed, (ii) a number of first-degree relatives of the subject that developed the disease of interest or indicator disease, and (iii) a number of second-degree relatives of the subject that developed the disease of interest or indicator disease.

* * * * *